US011584938B2

(12) United States Patent
Chen et al.

(10) Patent No.: US 11,584,938 B2
(45) Date of Patent: Feb. 21, 2023

(54) PLANT EPSPS MUTANT CONTAINING L195P AND S247G MUTATIONS AND ENCODING GENE AND USE THEREOF

(71) Applicant: GEVOTO LLC, Sichuan (CN)

(72) Inventors: Rong Chen, Sichuan (CN); Longqun Deng, Sichuan (CN); Qingjiang Hou, Sichuan (CN); Yuangen Lu, Sichuan (CN); Qian Ou, Sichuan (CN); Xiaorong Feng, Sichuan (CN); Ling Li, Sichuan (CN); Xin Huang, Sichuan (CN); Nanfei Xu, Sichuan (CN)

(73) Assignee: GEVOTO LLC, Sichuan (CN)

( * ) Notice: Subject to any disclaimer, the term of this patent is extended or adjusted under 35 U.S.C. 154(b) by 246 days.

(21) Appl. No.: 16/767,524

(22) PCT Filed: Dec. 14, 2018

(86) PCT No.: PCT/CN2018/121329
§ 371 (c)(1),
(2) Date: May 27, 2020

(87) PCT Pub. No.: WO2019/128745
PCT Pub. Date: Jul. 4, 2019

(65) Prior Publication Data

US 2021/0079417 A1 Mar. 18, 2021

(30) Foreign Application Priority Data

Dec. 25, 2017 (CN) ......................... 201711416358.2
Sep. 13, 2018 (CN) ......................... 201811070071.3

(51) Int. Cl.
*C12N 15/82* (2006.01)
*C12N 9/10* (2006.01)

(52) U.S. Cl.
CPC ....... *C12N 15/8275* (2013.01); *C12N 9/1092* (2013.01); *C12Y 205/01019* (2013.01)

(58) Field of Classification Search
CPC .................................................. C12N 15/8275
See application file for complete search history.

(56) References Cited

FOREIGN PATENT DOCUMENTS

| | | | |
|---|---|---|---|
| CN | 1810962 | A | 8/2006 |
| CN | 101864437 | A | 10/2010 |
| CN | 102399794 | A | 4/2012 |
| CN | 105063068 | A | 11/2015 |
| CN | 106636025 | A | 5/2017 |

OTHER PUBLICATIONS

Padgette et al, J. of Biol. Chem. (1991) 266:22364-22369.*
First Office Action dated May 30, 2019 in CN 201811070071.3, with English-language translation.
Second Office Action dated Aug. 12, 2019 in CN 201811070071.3, with English-language translation.
International Search Report dated Mar. 13, 2019 issued in PCT/CN2018/121329, with English-language translation.
Written Opinion dated Mar. 13, 2020 in PCT/CN2018/121329.
First Search of Priority Document No. CN 201811070071.3.
Notification of Grant issued in CN 201811070071.3, with English-language translation.
Chen et al., "Mutations and amplifications of EPSPS gene confer resistance to glyphosate in goosegrass (*Eleusine indica*)" Planta (2015) 242: 859-868.
CA Examination Report dated May 5, 2021 from CA Application Serial No. 3,083,031.
CA Examination Report dated Feb. 24, 2022 from CA Application Serial No. 3,083,031.

* cited by examiner

*Primary Examiner* — Mykola V. Kovalenko
(74) *Attorney, Agent, or Firm* — Hogan Lovells US LLP

(57) ABSTRACT

Provided are a plant EPSPS mutant containing mutations L195P and S247G and an encoding gene and the use thereof, related to the field of genetic engineering technology. Comparing the plant EPSPS mutant with *E. coli* EPSPS, the amino acid sequence of the plant EPSPS mutant has the mutation L195P at position 195 corresponding to *E. coli* EPSPS and/or the mutation S247G at position 247 corresponding to *E. coli* EPSPS. The mutation of either of the two sites or the simultaneous mutation of the two sites can confer or improve the resistance of the plant EPSPS mutant to glyphosate. Plants or recombinant bacteria for transforming the plant EPSPS mutant can grow normally in the presence of glyphosate.

8 Claims, 6 Drawing Sheets

Specification includes a Sequence Listing.

PLANT EPSPS MUTANT CONTAINING L195P AND S247G MUTATIONS AND ENCODING GENE AND USE THEREOF

CROSS-REFERENCE TO RELATED APPLICATION

This application is 35 U.S.C. § 371 National Stage Application of PCT/CN2018/121329, filed on Dec. 14, 2018, which application is herein incorporated by reference. The present disclosure claims the priorities to the Chinese patent application with the filing number 201711416358.2 filed on Dec. 25, 2017 with the Chinese Patent Office and entitled "Plant EPSPS Mutant Containing L195P and S247G Mutations and Encoding Gene and Use thereof" and the Chinese patent application with the filing number 201811070071.3 filed on Sep. 13, 2018 with the Chinese Patent Office and entitled "Plant EPSPS Mutant Containing L195P and S247G Mutations and Encoding Gene and Use thereof", which are incorporated herein by reference in entirety.

TECHNICAL FIELD

The present disclosure relates to the technical field of gene engineering, in particular to a plant EPSPS mutant containing L195P and S247G mutations, and an encoding gene and use thereof.

BACKGROUND ART

Glyphosate is one of the most common herbicides currently used in the world, and has been used for nearly 40 years up to now. Glyphosate inhibits activity of 5-enolpyruvylshikimate-3-phosphate synthase (EPSPS). EPSPS catalyzes PEP and shikimate-3-phosphate to synthesize EPSP in a shikimic acid pathway, and finally leads to the synthesis of aromatic amino acid tryptophan, phenylalanine and tyrosine. Glyphosate blocks the synthesis of these aromatic amino acids, thereby affecting normal growth of plants, and eventually causing death of affected plants.

At present, a main method for creating a glyphosate-resistant breed is to use gene engineering to transform a glyphosate-resistant gene derived from bacteria into the crop, thereby cultivating a new breed of transgenic glyphosate-resistant crop. Since the launch beginning in 1996, the cultivated area has increased quickly, and as of 2015, the cultivated area of the glyphosate-resistant transgenic crops in the world has reached 150 million hectares, accounting for 83% of total cultivated area of transgenic crops, and bringing huge benefits to agricultural production and environment.

However, the most widely used glyphosate-resistant gene currently in agriculture is CP4 EPSPS derived from *Agrobacterium tumefaciens* CP4 strain. Although many EPSPS genes capable of resisting glyphosate have been found from microorganisms, these genes have not been widely used in crops. To use glyphosate-resistant genes derived from these microorganisms in crops, these genes, e.g. CP4 EPSPS, are expressed in crops by transgenic methods. Although transgenic crops produced thereby have been commercialized at quite large area, public acceptance of transgenic crops is still a major issue around the globe, and even in America with the largest cultivated area of transgenic crops, the transgenic crops are mainly limited to a few crops such as maize, soybean, and cotton.

SUMMARY

An objective of the present disclosure is to provide a plant EPSPS mutant (i.e. 5-enolpyruvylshikimate-3-phosphate synthase mutant), which is derived from plant, and has glyphosate resistance after mutation.

Another objective of the present disclosure is to provide an encoding gene, which can encode the above plant EPSPS mutant.

Another objective of the present disclosure is to provide a vector containing the above encoding gene.

Another objective of the present disclosure is to provide a cell containing the above vector.

Another objective of the present disclosure is to provide use of the above plant EPSPS mutant.

The present disclosure is achieved as follows:

A plant EPSPS mutant, compared with an *E. coli* (*Escherichia coli*) EPSPS, the amino acid sequence of the plant EPSPS mutant contains a mutation L195P corresponding to a site 195 of the *E. coli* EPSPS and/or a mutation S247G corresponding to a site 247 of the *E. coli* EPSPS.

An encoding gene, which encodes the above plant EPSPS mutant.

A vector containing the above encoding gene.

A recombinant cell containing the above vector.

Use of the above plant EPSPS mutant in cultivation of glyphosate-resistant plants.

THE PRESENT DISCLOSURE HAS THE FOLLOWING BENEFICIAL EFFECTS

A plant EPSPS mutant provided in the present disclosure, compared with the *E. coli* (*Escherichia coli*) EPSPS, the amino acid sequence of the plant EPSPS mutant contains the mutation L195P corresponding to the site 195 of the *E. coli* EPSPS and/or the mutation S247G corresponding to the site 247 of the *E. coli* EPSPS. The mutation of either site of the two sites or simultaneous mutation of the two sites both can improve resistance of EPSPS mutants of multiple types of plant to glyphosate, and meanwhile maintain their own catalytic activity of biological enzyme. A plant or a recombinant bacterium transformed by the plant EPSPS mutant provided in the present disclosure can grow normally in the presence of glyphosate, and the plant EPSPS mutant not only can be used for cultivation of transgenic crop, but also can be used for cultivating glyphosate-resistant non-transgenic plants such as rice, tobacco, soybean, maize, wheat, cotton and sorghum, which has a broad application prospect.

SEQUENCE LISTING

The instant application contains a Sequence Listing which has been submitted electronically in ASCII format and is hereby incorporated by reference in its entirety. Said ASCII copy, created on Nov. 11, 2020, is named 046231_000043_SL.txt and is 126,336 bytes in size.

BRIEF DESCRIPTION OF DRAWINGS

In order to more clearly illustrate technical solutions of examples of the present disclosure, drawings which need to be used for the examples will be introduced briefly below, and it should be understood that the drawings below merely show some examples of the present disclosure, therefore, they should not be considered as limitation on the scope, and those ordinarily skilled in the art still could obtain other relevant drawings according to these drawings, without any creative effort.

DETAILED DESCRIPTION OF EMBODIMENTS

Figure 1:
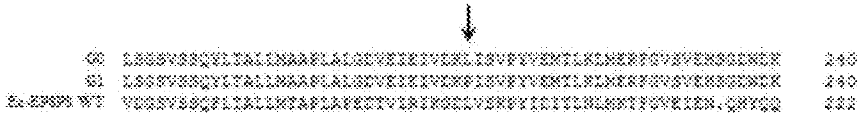
FIG. 1 shows partial alignment results of amino acid sequences of the three, namely, soybean EPSPS mutant G1 (SEQ ID NO: 4), wild-type soybean EPSPS (SEQ ID NO: 2), and *E. coli* EPSPS (SEQ ID NO: 41), provided in Example 1 of the present disclosure.

In order to make the objectives, technical solutions and advantages of the examples of the present disclosure clearer, the technical solutions in the examples of the present disclosure will be described below clearly and completely. If no specific conditions are specified in the examples, they are carried out under normal conditions or conditions recommended by manufacturers. If manufacturers of reagents or apparatuses used are not specified, they are conventional products commercially available.

A plant EPSPS mutant containing mutations L195P and S247G and an encoding gene and use thereof provided in examples of the present disclosure are specifically described below.

In one aspect, the present disclosure provides a plant EPSPS mutant, and compared with an *E. coli* EPSPS, the amino acid sequence of the plant EPSPS mutant contains a mutation L195P corresponding to a site 195 of the *E. coli* EPSPS and/or a mutation S247G corresponding to a site 247 of the *E. coli* EPSPS.

That is to say, the amino acid sequence of the plant EPSPS mutant provided in the present disclosure is aligned with an amino acid sequence of the *E. coli* EPSPS, an amino acid residue L of the amino acid sequence of the plant EPSPS mutant corresponding to the site 195 of the *E. coli* EPSPS (an amino acid residue of a wild-type plant EPSPS corresponding to this site is L) is mutated to P, or an amino acid residue S corresponding to the site 247 of the *E. coli* EPSPS (i.e., the amino acid residue of the wild-type plant EPSPS corresponding to this site is S) is mutated to G.

Of course, the plant EPSPS mutant provided in the present disclosure also can simultaneously contain the two mutations above.

In other words, the plant EPSPS mutant provided in the present disclosure is obtained through following mutations:

(1) aligning the amino acid sequence of the wild-type plant EPSPS with the amino acid sequence of the *E. coli* EPSPS, and mutating the amino acid residue L of the wild-type plant EPSPS corresponding to the site 195 of the *E. coli* EPSPS to P, to obtain the plant EPSPS mutant having glyphosate resistance provided in the present disclosure; or (2) aligning the amino acid sequence of the wild-type plant EPSPS with the amino acid sequence of the *E. coli* EPSPS, and mutating the amino acid residue S of the wild-type plant EPSPS corresponding to the site 247 of the *E. coli* EPSPS to G, to obtain the plant EPSPS mutant having glyphosate resistance provided in the present disclosure; or (3) aligning the amino acid sequence of the wild-type plant EPSPS with the amino acid sequence of the *E. coli* EPSPS, and mutating the amino acid residue L of the wild-type plant EPSPS corresponding to the site 195 of the *E. coli* EPSPS to P and mutating the amino acid residue S of the wild-type plant EPSPS corresponding to the site 247 of the *E. coli* EPSPS to G, to obtain the plant EPSPS mutant having glyphosate resistance provided in the present disclosure.

It should be indicated that specific sites of mutation sites of the wild-type plant EPSPS corresponding to the site 195 and the site 247 of the *E. coli* EPSPS on the wild-type plant EPSPS sequence are different due to different species sources.

Further, in some embodiments of the present disclosure, the amino acid sequence of the plant EPSPS mutant further contains a mutation P101S corresponding to the site 101 of the *E. coli* EPSPS.

That is to say, the amino acid sequence of the plant EPSPS mutant provided in the present disclosure is aligned with the amino acid sequence of the *E. coli* EPSPS, and the amino acid residue P of the amino acid sequence of the plant EPSPS mutant corresponding to the site 101 of the *E. coli* EPSPS (i.e., the amino acid residue of the wild-type plant EPSPS corresponding to this site is P) is mutated to S.

Further, in some embodiments of the present disclosure, the plant EPSPS mutant is derived from any one of wheat, rice, barley, oat, maize, sorghum, millet, buckwheat, maiden cane, mung bean, broad bean, pea, lentil, sweet potato, potato, cotton, soybean, rape plant, sesame, peanut, sunflower, radish, carrot, turnip, beet, Chinese cabbage, mustard, cabbage, cauliflower, Chinese kale, cucumber, zucchini, pumpkin, wax gourd, balsam pear, loofah, snake melon, watermelon, melon, tomato, eggplant, pepper, kidney bean, cowpea, green soy bean, Chinese chives, welsh onion, onion, leek, spinach, celery, amaranth, lettuce, crowndaisy *chrysanthemum*, daylily, grape, strawberry, beet, sugarcane, tobacco, alfalfa, pasture grass, turfgrass, tea and cassava.

The plant EPSPS mutant provided in the present disclosure is obtained after the above mutation of wild-type EPSPS derived from plants such as rice, tobacco, soybean, maize, wheat, cotton, rape plant and sorghum, and it maintains the plant source characteristics. An encoding gene encoding this plant EPSPS mutant can be applied to the cultivation of glyphosate-resistant crop varieties, for example, a transgenic or genetic modification method can be adopted to realize the cultivation purpose. Compared with the existing mode of transforming the glyphosate-resistant genes derived from microorganisms, directly transforming the glyphosate-resistant genes from plant sources or editing the gene with the glyphosate-resistant genes from plant sources as a template has more reliable biological safety, which is favorable for the popularization and the application of new glyphosate-resistant varieties, and improves the public acceptance.

Further, in some embodiments of the present disclosure, the amino acid sequence of the *E. coli* EPSPS is represented by SEQ ID NO: 41.

Further, in some embodiments of the present disclosure, the amino acid sequence of the EPSPS mutant is any one selected from the following sequences:

SEQ ID NO: 4, SEQ ID NO: 8, SEQ ID NO: 10, SEQ ID NO: 12, SEQ ID NO: 16, SEQ ID NO: 20, SEQ ID NO: 22, SEQ ID NO: 24, SEQ ID NO: 26, SEQ ID NO: 30, SEQ ID NO: 34, SEQ ID NO: 36, SEQ ID NO: 38 and SEQ ID NO: 40.

In the above, the EPSPS mutants represented by SEQ ID NO: 4, SEQ ID NO: 8, SEQ ID NO: 10 and SEQ ID NO: 12 are obtained by mutating the wild-type soybean EPSPS (SEQ ID NO: 2) derived from soybean (*Glycine max* (Linn.) Merr.) at mutation sites resistant to glyphosate, wherein the mutation sites resistant to glyphosate include sites corresponding to the site 195, the site 247 and the site 101 of the *E. coli* represented by SEQ ID NO: 41.

For example, the soybean EPSPS mutant (named as G1) represented by SEQ ID NO: 4 contains the mutation L195P corresponding to the site 195 of the *E. coli* EPSPS, and this site is corresponding to the site 212 of the wild-type soybean EPSPS (such mutation also can be denoted by L212(195)P);

The soybean EPSPS mutant (named as G3) represented by SEQ ID NO: 8 contains the mutation L195P (denoted by L212(195)P) corresponding to the site 195 of the *E. coli* EPSPS, and contains the mutation P101S (denoted by P114 (101)S) corresponding to the site 101 of the *E. coli* EPSPS, and this site is corresponding to the site 114 of the wild-type soybean EPSPS;

The soybean EPSPS mutant (named as G4) represented by SEQ ID NO: 10 contains the mutation S247G corresponding to the site 247 of the *E. coli* EPSPS, and this site is corresponding to the site 265 of the wild-type soybean EPSPS (such mutation also can be denoted by S265(247)G);

The EPSPS mutant (named as G5) represented by SEQ ID NO: 12 contains the mutation S247G (denoted by S265(247) G) corresponding to the site 247 of the *E. coli* EPSPS, and contains the mutation P101S (denoted by P114(101)S) corresponding to the site 101 of the *E. coli* EPSPS, and this site is corresponding to the site 114 of the wild-type soybean EPSPS. Besides, the EPSPS mutants represented by SEQ ID NO: 16, SEQ ID NO: 20, SEQ ID NO: 22, SEQ ID NO: 24 and SEQ ID NO: 26 are obtained by mutating the wild-type wheat EPSPS (SEQ ID NO: 14) derived from wheat (*Triticum aestivum* L) at mutation sites resistant to glyphosate, wherein the mutation sites resistant to glyphosate include sites corresponding to the site 195, the site 247 and the site 101 of the *E. coli* represented by SEQ ID NO: 41.

For example, the wheat EPSPS mutant (named as T1) represented by SEQ ID NO: 16 contains the mutation S247G corresponding to the site 247 of the *E. coli* EPSPS, and this site is corresponding to the site 269 of the wild-type wheat EPSPS (SEQ ID NO: 14) (such mutation also can be denoted by S269(247)G);

The wheat EPSPS mutant (named as T3) represented by SEQ ID NO: 20 contains the mutation S247G (i.e. S269(247)G) corresponding to the site 247 of the *E. coli* EPSPS, and contains the mutation P101S (which can be denoted by P118(101)S) corresponding to the site 101 of the *E. coli* EPSPS, and this site is corresponding to the site 118 of the wild-type wheat EPSPS;

The wheat EPSPS mutant (named as T4) represented by SEQ ID NO: 22 contains the mutation L195P corresponding to the site 195 of the *E. coli* EPSPS, and this site is corresponding to the site 216 of the wild-type wheat EPSPS (such mutation also can be denoted by L216(195)P);

The wheat EPSPS mutant (named as T5) represented by SEQ ID NO: 24 contains the mutation L195P (i.e. L216(195)P) corresponding to the site 195 of the *E. coli* EPSPS, and contains the mutation S247G (i.e. S269(247)G) corresponding to the site 247 of the *E. coli* EPSPS;

The wheat EPSPS mutant (named as T6) represented by SEQ ID NO: 26 contains the mutation L195P (i.e. L216(195)P) corresponding to the site 195 of the *E. coli* EPSPS, the mutation S247G (i.e. S269(247)G) corresponding to the site 247 of the *E. coli* EPSPS, and the mutation P101S (i.e. P118(101)S) corresponding to the site 101 of the *E. coli* EPSPS.

Besides, the EPSPS mutants represented by SEQ ID NO: 30, SEQ ID NO: 34, SEQ ID NO: 36, SEQ ID NO: 38 and SEQ ID NO: 40 are obtained by mutating the wild-type rice EPSPS (SEQ ID NO: 28) derived from rice (*Oryza sativa*) at mutation sites resistant to glyphosate, wherein the mutation sites resistant to glyphosate include sites corresponding to the site 195, the site 247 and the site 101 of the *E. coli* represented by SEQ ID NO: 41.

For example, the rice EPSPS mutant (named as R1) represented by SEQ ID NO: 30 contains the mutation L195P corresponding to the site 195 of the *E. coli* EPSPS, and this site is corresponding to the site 214 of the wild-type rice EPSPS (SEQ ID NO: 28) (mutation at such site can be denoted by L214(195)P);

The rice EPSPS mutant (named as R3) represented by SEQ ID NO: 34 contains the mutation L195P (i.e. L214(195)P) corresponding to the site 195 of the *E. coli* EPSPS, and contains the mutation P101S corresponding to the site 101 of the *E. coli* EPSPS, and this site is corresponding to the site 116 of the wild-type rice EPSPS (mutation at such site also can be denoted by P116(101)S);

The rice EPSPS mutant (named as R4) represented by SEQ ID NO: 36 contains the mutation S247G corresponding to the site 247 of the *E. coli* EPSPS, and this mutation site is corresponding to the site 267 of the wild-type rice EPSPS (mutation at such site can be denoted by S267(247)G);

The rice EPSPS mutant (named as R5) represented by SEQ ID NO: 38 contains the mutation S247G (i.e. S267(247)G) corresponding to the site 247 of the *E. coli* EPSPS, and contains the mutation P101S (i.e. P116(101)S) corresponding to the site 101 of the *E. coli* EPSPS;

The rice EPSPS mutant (named as R6) represented by SEQ ID NO: 40 contains the mutation S247G (i.e. S267(247)G) corresponding to the site 247 of the *E. coli* EPSPS, the mutation L195P (i.e. L214(195)P) corresponding to the site 195 of the *E. coli* EPSPS, and the mutation P101S (i.e. P116(101)S) corresponding to site 101 of the *E. coli* EPSPS.

Compared with the *E. coli* EPSPS (SEQ ID NO: 41), all the above plant EPSPS mutants containing a single mutation L195P or S247G, or simultaneously containing the mutation L195P and the mutation S247G, represented by SEQ ID NO: 4, SEQ ID NO: 8, SEQ ID NO: 10, SEQ ID NO: 12, SEQ ID NO: 16, SEQ ID NO: 20, SEQ ID NO: 22, SEQ ID NO: 24, SEQ ID NO: 26, SEQ ID NO: 30, SEQ ID NO: 34, SEQ ID NO: 36, SEQ ID NO: 38 and SEQ ID NO: 40 have glyphosate resistance, and the *E. coli* and the plant transformed by these EPSPS mutants can grow normally in the presence of glyphosate.

In another aspect, the present disclosure further provides an encoding gene, which encodes the plant EPSPS mutant described above.

Further, a base sequence of these encoding genes is any one selected from following sequences:

SEQ ID NO: 3, SEQ ID NO: 7, SEQ ID NO: 9, SEQ ID NO: 11, SEQ ID NO: 15, SEQ ID NO: 19, SEQ ID NO: 21, SEQ ID NO: 23, SEQ ID NO: 25, SEQ ID NO: 29, SEQ ID NO: 33, SEQ ID NO: 35, SEQ ID NO: 37 and SEQ ID NO: 39.

In the above,

SEQ ID NO: 3 encodes the soybean EPSPS mutant G1 represented by SEQ ID NO: 4;

SEQ ID NO: 7 encodes the soybean EPSPS mutant G3 represented by SEQ ID NO: 8;

SEQ ID NO: 9 encodes the soybean EPSPS mutant G4 represented by SEQ ID NO: 10;

SEQ ID NO: 11 encodes the soybean EPSPS mutant G5 represented by SEQ ID NO: 12;

SEQ ID NO: 15 encodes the wheat EPSPS mutant T1 represented by SEQ ID NO: 16;

SEQ ID NO: 19 encodes the wheat EPSPS mutant T3 represented by SEQ ID NO: 20;

SEQ ID NO: 21 encodes the wheat EPSPS mutant T4 represented by SEQ ID NO: 22;

SEQ ID NO: 23 encodes the wheat EPSPS mutant T5 represented by SEQ ID NO: 24;

SEQ ID NO: encodes the wheat EPSPS mutant T6 represented by SEQ ID NO: 26;

SEQ ID NO: 29 encodes the rice EPSPS mutant R1 represented by SEQ ID NO: 30;

SEQ ID NO: 33 encodes the rice EPSPS mutant R3 represented by SEQ ID NO: 34;

SEQ ID NO: 35 encodes the rice EPSPS mutant R4 represented by SEQ ID NO: 36;

SEQ ID NO: 37 encodes the rice EPSPS mutant R5 represented by SEQ ID NO: 38; and SEQ ID NO: 39 encodes the rice EPSPS mutant R6 represented by SEQ ID NO: 40.

It should be easily understood that a person skilled in the art, according to degeneracy of codon, could easily substitute one or more nucleotides on the basis of sequences of the above encoding genes, to obtain corresponding derivative sequences, such that the plant EPSPS mutant provided in the present disclosure is encoded. Therefore, substituting one or more nucleotides on the basis of sequences of the above encoding genes to obtain corresponding derivative sequences encoding the plant EPSPS mutant provided in the present disclosure also falls into the scope of protection of the present disclosure.

In another aspect, the present disclosure further provides a vector containing the encoding gene as described above.

Further, in some embodiments of the present disclosure, the vector may be a cloning vector or an expression vector, and further, in some embodiments of the present disclosure, the expression vector may be a prokaryotic expression vector, for example, pADV5 vector, or a eukaryotic expression vector. Further, in some embodiments of the present disclosure, the eukaryotic expression vector is a plant expression vector, for example, pGVP1 vector.

It is easily understood that a person skilled in the art could select a suitable vector as a tool for carrying the above encoding genes according to needs, which falls within the scope of protection of the present disclosure.

In another aspect, the present disclosure provides a recombinant bacterium or a recombinant cell containing the above vector.

Further, in some embodiments of the present disclosure, the recombinant bacterium may be a coccus, a *bacillus*, for example, *E. coli*, or a *Helicobacter*; it also may be an autotrophic bacterium or a heterotrophic bacterium.

Further, in some embodiments of the present disclosure, the recombinant cell may be a prokaryotic cell or a eukaryotic cell; further, in some embodiments of the present disclosure, the eukaryotic cell may be an animal cell, or may be a plant cell; further, in some embodiments of the present disclosure, the plant cell may be a dicotyledonous plant cell or a monocotyledonous plant cell.

It is easily understood that a person skilled in the art could select a suitable bacterium or cell as a host of the above encoding genes according to needs, which falls into the scope of protection of the present disclosure.

In another aspect, the present disclosure provides use of the above plant EPSPS mutant in cultivation of glyphosate-resistant plants.

Further, in some embodiments of the present disclosure, the above use includes: transforming a target plant with a vector, wherein the vector contains an encoding gene that encodes the plant EPSPS mutant.

For example, a complete rice plant is formed by transforming a cell, e.g. rice callus, with a vector containing a gene that encodes the rice EPSPS mutant represented by SEQ ID NO: 29, SEQ ID NO: 33, SEQ ID NO: 35, SEQ ID NO: 37, or SEQ ID NO: 39, and culturing to make the transformed rice callus differentiated, then the transgenic glyphosate-resistant rice can be cultivated. The transgenic rice plant transformed by such encoding gene does not introduce an exogenous gene, i.e. a gene of different species, then the degree of public acceptance can be improved.

Further, in some embodiments of the present disclosure, the above use includes: modifying an endogenous EPSPS gene of a target plant such that the plant EPSPS mutant is encoded.

For example, a non-transgenic rice can be cultivated by modifying the endogenous EPSPS gene of the rice genome with a part or all of the gene encoding the rice EPSPS mutant represented by SEQ ID NO: 29, SEQ ID NO: 33, SEQ ID NO: 35, SEQ ID NO: 37, or SEQ ID NO: 39 as a template.

Further, in some embodiments of the present disclosure, the above use includes: carrying out mutagenesis and screening in a plant cell, tissue, individual or population such that the plant EPSPS mutant is encoded.

For example, mutagenesis, such as chemical mutagenesis and radiation mutagenesis, is carried out to the rice material, with the gene encoding the R6 mutant represented by SEQ ID NO: 39 as a guide, and then rice with endogenous EPSPS gene mutation can be cultivated. For example, an encoding sequence of the endogenous EPSPS gene further can be modified to a base sequence (SEQ ID NO: 39) of the encoding gene through CRISPR/Cas9 technology, and the same protein as the rice R6 mutant (SEQ ID NO: 40) provided in the present disclosure is encoded in the target plant obtained, such that the target plant finally formed has glyphosate resistance.

Further, in some embodiments of the present disclosure, the target plant is any one selected from the group consisting of wheat, rice, barley, oat, maize, sorghum, millet, buckwheat, maiden cane, mung bean, broad bean, pea, lentil, sweet potato, potato, cotton, soybean, rape plant, sesame, peanut, sunflower, radish, carrot, turnip, beet, Chinese cabbage, mustard, cabbage, cauliflower, Chinese kale, cucumber, zucchini, pumpkin, wax gourd, balsam pear, loofah, snake melon, watermelon, melon, tomato, eggplant, pepper, kidney bean, cowpea, green soy bean, Chinese chives, welsh onion, onion, leek, spinach, celery, amaranth, lettuce, crowndaisy *chrysanthemum*, daylily, grape, strawberry, beet, sugarcane, tobacco, alfalfa, pasture grass, turfgrass, tea and cassava.

It is easily understood that a person skilled in the art could select the crop variety required to be cultivated according to the needs, which fall within the scope of protection of the present disclosure as long as the plant EPSPS mutant and/or the encoding gene thereof provided in the present disclosure are/is applied.

It should be indicated that, the alignment method used in the protein sequence alignment involved in the present disclosure is Clustal online alignment. Results obtained by using other sequence alignment tools (e.g., DNAMAN, with relevant parameter settings set by default) are substantially identical to that obtained by the Clustal online alignment.

To sum up, the present disclosure provides the EPSPS mutant, for example, SEQ ID NO: 4, SEQ ID NO: 8, SEQ ID NO: 10, SEQ ID NO: 12, SEQ ID NO: 16, SEQ ID NO: 20, SEQ ID NO: 22, SEQ ID NO: 24, SEQ ID NO: 26, SEQ ID NO: 30, SEQ ID NO: 34, SEQ ID NO: 36, SEQ ID NO: 38 or SEQ ID NO: 40, and compared with *E. coli* EPSPS, the amino acid sequence of the plant EPSPS mutant contains the mutation L195P corresponding to the site 195 of the *E. coli* EPSPS (SEQ ID NO: 41) and/or the mutation S247G corresponding to the site 247 of the *E. coli* EPSPS (SEQ ID NO: 41).

The mutation of either site of the two sites or simultaneous mutation of the two sites both can improve resistance of EPSPS mutants of multiple types of plant to glyphosate, and meanwhile maintain their own catalytic activity of biological enzyme. A plant or a recombinant bacterium transformed by the plant EPSPS mutant provided in the present disclosure can grow normally in the presence of glyphosate, and the plant EPSPS mutant not only can be used for cultivation of transgenic crop, but also can be used for cultivating glyphosate-resistant non-transgenic plants such as rice, tobacco, soybean, maize, wheat, cotton and sorghum, which has a broad application prospect.

The features and performances of the present disclosure are further described below in detail in combination with examples.

EXAMPLES

Example 1

A soybean EPSPS mutant provided in the present example, named as G1, has an amino acid sequence represented by SEQ ID NO: 4.

The soybean EPSPS mutant G1 provided in the present example is obtained by mutating an amino acid residue L of a wild-type soybean EPSPS (named as G0, with an amino acid sequence represented by SEQ ID NO: 2) corresponding to a site 195 (this mutation site is located at a site 212 of the wild-type soybean EPSPS) of an *E. coli* EPSPS (with an amino acid sequence represented by SEQ ID NO: 41) to P.

The amino acid sequences of the three, namely, the soybean EPSPS mutant G1, the wild-type soybean EPSPS and the *E. coli* EPSPS, are aligned as shown in FIG. 1, wherein a position indicated by an arrow is a mutation site, and Ec-EPSPS WT represents the *E. coli* EPSPS.

Besides, the present example further provides a nucleic acid molecule (i.e. encoding gene) encoding the soybean EPSPS mutant G1, which has a base sequence represented by SEQ ID NO: 3.

The soybean EPSPS mutant G1 and the nucleic acid molecule encoding the soybean EPSPS mutant G1 provided in the present example both can be obtained through a chemical synthesis method.

Example 2

A soybean EPSPS mutant provided in the present example, named as G3, has an amino acid sequence represented by SEQ ID NO: 8.

The soybean EPSPS mutant G3 provided in the present example is obtained by mutating an amino acid residue L of a wild-type soybean EPSPS (named as G0, with an amino acid sequence represented by SEQ ID NO: 2) corresponding to a site 195 (this mutation site is located at a site 212 of the wild-type soybean EPSPS) of an *E. coli* EPSPS (with an amino acid sequence represented by SEQ ID NO: 41) to P and mutating an amino acid residue P of the wild-type soybean EPSPS corresponding to a site 101 (this site is corresponding to a site 114 of the wild-type soybean EPSPS) of the *E. coli* EPSPS to S.

Figure 2:
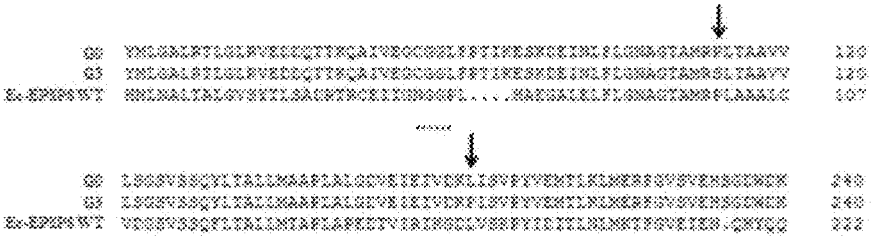
FIG. 2 shows partial alignment results of amino acid sequences of the three, namely, soybean EPSPS mutant G3 (SEQ ID NO: 8), wild-type soybean EPSPS (SEQ ID NO: 2), and *E. coli* EPSPS (SEQ ID NO: 41), provided in Example 2 of the present disclosure.

The amino acid sequences of the three, namely, the soybean EPSPS mutant G3, the wild-type soybean EPSPS and the *E. coli* EPSPS, are aligned as shown in FIG. 2, wherein a position indicated by an arrow is a mutation site, and Ec-EPSPS WT represents the *E. coli* EPSPS.

Besides, the present example further provides a nucleic acid molecule encoding the soybean EPSPS mutant G3, which has a base sequence represented by SEQ ID NO: 7.

The soybean EPSPS mutant G3 and the nucleic acid molecule encoding the soybean EPSPS mutant G3 provided in the present example both can be obtained through a chemical synthesis method.

Example 3

A soybean EPSPS mutant provided in the present example, named as G4, has an amino acid sequence represented by SEQ ID NO: 10.

The soybean EPSPS mutant G4 provided in the present example is obtained by mutating an amino acid residue S of a wild-type soybean EPSPS (named as G0, with an amino acid sequence represented by SEQ ID NO: 2) corresponding to a site 247 (this site is corresponding to a site 265 of the wild-type soybean EPSPS) of an *E. coli* EPSPS (with an amino acid sequence represented by SEQ ID NO: 41) to G.

Figure 3:
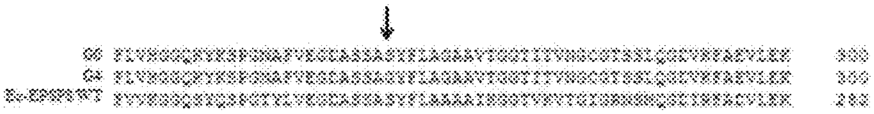
FIG. 3 shows partial alignment results of amino acid sequences of the three, namely, soybean EPSPS mutant G4 (SEQ ID NO: 10), wild-type soybean EPSPS (SEQ ID NO: 2), and *E. coli* EPSPS (SEQ ID NO: 41), provided in Example 3 of the present disclosure.

The amino acid sequences of the three, namely, the soybean EPSPS mutant G4, the wild-type soybean EPSPS and the *E. coli* EPSPS, are aligned as shown in FIG. 3, wherein a position indicated by an arrow is a mutation site, and Ec-EPSPS WT represents the *E. coli* EPSPS.

Besides, the present example further provides a nucleic acid molecule encoding the soybean EPSPS mutant G4, which has a base sequence represented by SEQ ID NO: 9.

The soybean EPSPS mutant G4 and the nucleic acid molecule encoding the soybean EPSPS mutant G4 provided in the present example both can be obtained through a chemical synthesis method.

Example 4

A soybean EPSPS mutant provided in the present example, named as G5, has an amino acid sequence represented by SEQ ID NO: 12.

The soybean EPSPS mutant G5 provided in the present example is obtained by mutating an amino acid residue S of a wild-type soybean EPSPS (named as G0, with an amino acid sequence represented by SEQ ID NO: 2) corresponding to a site 247 (this site is corresponding to a site 265 of the wild-type soybean EPSPS) of an *E. coli* EPSPS (with an amino acid sequence represented by SEQ ID NO: 41) to G and mutating an amino acid residue P of the wild-type soybean EPSPS corresponding to a site 101 (this site is corresponding to a site 114 of the wild-type soybean EPSPS) of the *E. coli* EPSPS to S.

Figure 4:
FIG. 4 shows partial alignment results of amino acid sequences of the three, namely, soybean EPSPS mutant G5 (SEQ ID NO: 12), wild-type soybean EPSPS (SEQ ID NO: 2), and *E. coli* EPSPS (SEQ ID NO: 41), provided in Example 4 of the present disclosure.

The amino acid sequences of the three, namely, the soybean EPSPS mutant G5, the wild-type soybean EPSPS and the *E. coli* EPSPS, are aligned as shown in FIG. 4, wherein a position indicated by an arrow is a mutation site, and Ec-EPSPS WT represents the *E. coli* EPSPS.

Besides, the present example further provides a nucleic acid molecule encoding the soybean EPSPS mutant G5, which has a base sequence represented by SEQ ID NO: 11.

The soybean EPSPS mutant G5 and the nucleic acid molecule encoding the soybean EPSPS mutant G5 provided in the present example both can be obtained through a chemical synthesis method.

Example 5

A wheat EPSPS mutant provided in the present example, named as T1, has an amino acid sequence represented by SEQ ID NO: 16.

The wheat EPSPS mutant T1 provided in the present example is obtained by mutating an amino acid residue S of a wild-type wheat EPSPS (named as T0, with an amino acid sequence represented by SEQ ID NO: 14) corresponding to a site 247 (this site is corresponding to a site 269 of the wild-type wheat EPSPS) of an *E. coli* EPSPS (with an amino acid sequence represented by SEQ ID NO: 41) to G.

Figure 5:
FIG. 5 shows partial alignment results of amino acid sequences of the three, namely, wheat EPSPS mutant T1 (SEQ ID NO: 16), wild-type wheat EPSPS (SEQ ID NO: 14) and *E. coli* EPSPS (SEQ ID NO: 41) provided in Example 5 of the present disclosure.

The amino acid sequences of the three, namely, the wheat EPSPS mutant T1, the wild-type wheat EPSPS and the *E. coli* EPSPS, are aligned as shown in FIG. 5, wherein a position indicated by an arrow is a mutation site, and Ec-EPSPS WT represents the *E. coli* EPSPS.

Besides, the present example further provides a nucleic acid molecule encoding the wheat EPSPS mutant T1, which has a base sequence represented by SEQ ID NO: 15.

The wheat EPSPS mutant T1 and the nucleic acid molecule encoding the wheat EPSPS mutant T1 provided in the present example both can be obtained through a chemical synthesis method.

Example 6

A wheat EPSPS mutant provided in the present example, named as T3, has an amino acid sequence represented by SEQ ID NO: 20.

The wheat EPSPS mutant T3 provided in the present example is obtained by mutating an amino acid residue S of a wild-type wheat EPSPS (named as T0, with an amino acid sequence represented by SEQ ID NO: 14) corresponding to a site 247 (this site is corresponding to a site 269 of the wild-type wheat EPSPS) of an *E. coli* EPSPS (with an amino acid sequence represented by SEQ ID NO: 41) to G and mutating an amino acid residue P of the wild-type wheat EPSPS corresponding to a site 101 (this site is corresponding to a site 118 of the wild-type wheat EPSPS) of the *E. coli* EPSPS to S.

Figure 6:
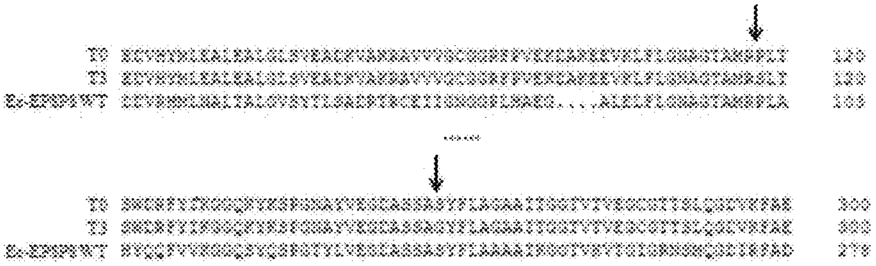
FIG. 6 shows partial alignment results of amino acid sequences of the three, namely, wheat EPSPS mutant T3 (SEQ ID NO: 20), wild-type wheat EPSPS (SEQ ID NO: 14) and *E. coli* EPSPS (SEQ ID NO: 41) provided in Example 6 of the present disclosure.

The amino acid sequences of the three, namely, the wheat EPSPS mutant T3, the wild-type wheat EPSPS and the *E. coli* EPSPS, are aligned as shown in FIG. 6, wherein a position indicated by an arrow is a mutation site, and Ec-EPSPS WT represents the *E. coli* EPSPS.

Besides, the present example further provides a nucleic acid molecule encoding the wheat EPSPS mutant T3, which has a base sequence represented by SEQ ID NO: 19.

The wheat EPSPS mutant T3 and the nucleic acid molecule encoding the wheat EPSPS mutant T3 provided in the present example both can be obtained through a chemical synthesis method.

Example 7

A wheat EPSPS mutant provided in the present example, named as T4, has an amino acid sequence represented by SEQ ID NO: 22.

The wheat EPSPS mutant T4 provided in the present example is obtained by mutating an amino acid residue L of a wild-type wheat EPSPS (named as T0, with an amino acid sequence represented by SEQ ID NO: 14) corresponding to the site 195 (this site is corresponding to a site 216 of the wild-type wheat EPSPS) of an *E. coli* EPSPS (with an amino acid sequence represented by SEQ ID NO: 41) to P.

Figure 7:
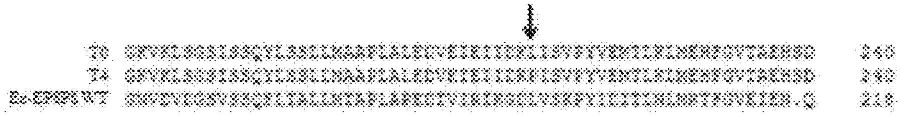
FIG. 7 shows partial alignment results of amino acid sequences of the three, namely, wheat EPSPS mutant T4 (SEQ ID NO: 22), wild-type wheat EPSPS (SEQ ID NO: 14) and *E. coli* EPSPS (SEQ ID NO: 41) provided in Example 7 of the present disclosure.

The amino acid sequences of the three, namely, the wheat EPSPS mutant T4, the wild-type wheat EPSPS and the *E. coli* EPSPS, are aligned as shown in FIG. 7, wherein a position indicated by an arrow is a mutation site, and Ec-EPSPS WT represents the *E. coli* EPSPS.

Besides, the present example further provides a nucleic acid molecule encoding the wheat EPSPS mutant T4, which has a base sequence represented by SEQ ID NO: 21.

The wheat EPSPS mutant T4 and the nucleic acid molecule encoding the wheat EPSPS mutant T4 provided in the present example both can be obtained through a chemical synthesis method.

Example 8

A wheat EPSPS mutant provided in the present example, named as T5, has an amino acid sequence represented by SEQ ID NO: 24.

The wheat EPSPS mutant T5 provided in the present example is obtained by mutating an amino acid residue S of a wild-type wheat EPSPS (named as T0, with an amino acid sequence represented by SEQ ID NO: 14) corresponding to a site 247 (this site is corresponding to a site 269 of the wild-type wheat EPSPS) of an *E. coli* EPSPS (with an amino acid sequence represented by SEQ ID NO: 41) to G and mutating an amino acid residue L of the wild-type wheat EPSPS corresponding to a site 195 (this site is corresponding to a site 216 of the wild-type wheat EPSPS) of the *E. coli* EPSPS to P.

Figure 8:
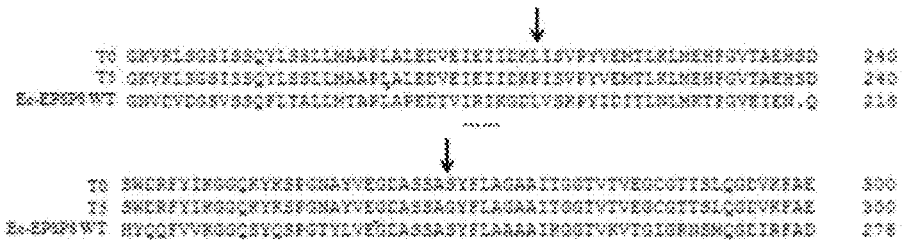
FIG. 8 shows partial alignment results of amino acid sequences of the three, namely, wheat EPSPS mutant T5 (SEQ ID NO: 24), wild-type wheat EPSPS (SEQ ID NO: 14) and *E. coli* EPSPS (SEQ ID NO: 41) provided in Example 8 of the present disclosure.

The amino acid sequences of the three, namely, the wheat EPSPS mutant T5, the wild-type wheat EPSPS and the *E. coli* EPSPS, are aligned as shown in FIG. 8, wherein a position indicated by an arrow is a mutation site, and Ec-EPSPS WT represents the *E. coli* EPSPS.

Besides, the present example further provides a nucleic acid molecule encoding the wheat EPSPS mutant T5, which has a base sequence represented by SEQ ID NO: 23.

The wheat EPSPS mutant T5 and the nucleic acid molecule encoding the wheat EPSPS mutant T5 provided in the present example both can be obtained through a chemical synthesis method.

Example 9

A wheat EPSPS mutant provided in the present example, named as T6, has an amino acid sequence represented by SEQ ID NO: 26.

The wheat EPSPS mutant T6 provided in the present example is obtained by mutating an amino acid residue P of a wild-type wheat EPSPS (named as T0, with an amino acid sequence represented by SEQ ID NO: 14) corresponding to a site 101 (this site is corresponding to a site 118 of the wild-type wheat EPSPS) of an *E. coli* EPSPS (with an amino acid sequence represented by SEQ ID NO: 41) to S, mutating an amino acid residue L of the wild-type wheat EPSPS corresponding to a site 195 (this site is corresponding to a site 216 of the wild-type wheat EPSPS) of the *E. coli* EPSPS to P and mutating an amino acid residue S of the wild-type wheat EPSPS corresponding to a site 247 (this site is corresponding to a site 269 of the wild-type wheat EPSPS) of the *E. coli* EPSPS to G.

Figure 9:
FIG. 9 shows partial alignment results of amino acid sequences of the three, namely, wheat EPSPS mutant T6 (SEQ ID NO: 26), wild-type wheat EPSPS (SEQ ID NO: 14) and *E. coli* EPSPS (SEQ ID NO: 41) provided in Example 9 of the present disclosure.

The amino acid sequences of the three, namely, the wheat EPSPS mutant T6, the wild-type wheat EPSPS and the *E. coli* EPSPS, are aligned as shown in FIG. 9, wherein a position indicated by an arrow is a mutation site, and Ec-EPSPS WT represents the *E. coli* EPSPS.

Besides, the present example further provides a nucleic acid molecule encoding the wheat EPSPS mutant T6, which has a base sequence represented by SEQ ID NO: 25.

The wheat EPSPS mutant T6 and the nucleic acid molecule encoding the wheat EPSPS mutant T6 provided in the present example both can be obtained through a chemical synthesis method.

Example 10

A rice EPSPS mutant provided in the present example, named as R1, has an amino acid sequence represented by SEQ ID NO: 30.

The rice EPSPS mutant R1 provided in the present example is obtained by mutating an amino acid residue L of a wild-type rice EPSPS (named as R0, with an amino acid sequence represented by SEQ ID NO: 28) corresponding to a site 195 (this site is corresponding to a site 214 of the wild-type rice EPSPS) of an *E. coli* EPSPS (with an amino acid sequence represented by SEQ ID NO: 41) to P.

Figure 10:
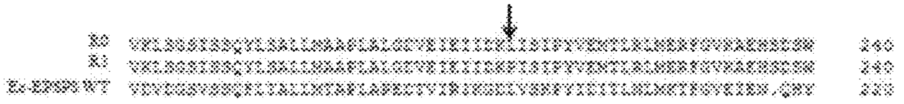
FIG. 10 shows partial alignment results of amino acid sequences of the three, namely, rice EPSPS mutant R1 (SEQ ID NO: 30), wild-type rice EPSPS (SEQ ID NO: 28) and *E. coli* EPSPS (SEQ ID NO: 41) provided in Example 10 of the present disclosure.

The amino acid sequences of the three, namely, the rice EPSPS mutant R1, the wild-type rice EPSPS and the *E. coli* EPSPS, are aligned as shown in FIG. 10, wherein a position indicated by an arrow is a mutation site, and Ec-EPSPS WT represents the *E. coli* EPSPS.

Besides, the present example further provides a nucleic acid molecule encoding the rice EPSPS mutant R1, which has a base sequence represented by SEQ ID NO: 29.

The rice EPSPS mutant R1 and the nucleic acid molecule encoding the rice EPSPS mutant R1 provided in the present example both can be obtained through a chemical synthesis method.

Example 11

A rice EPSPS mutant provided in the present example, named as R3, has an amino acid sequence represented by SEQ ID NO: 34.

The rice EPSPS mutant R3 provided in the present example is obtained by mutating an amino acid residue L of a wild-type rice EPSPS (named as R0, with an amino acid sequence represented by SEQ ID NO: 28) corresponding to a site 195 (this site is corresponding to a site 214 of the wild-type rice EPSPS) of an *E. coli* EPSPS (with an amino acid sequence represented by SEQ ID NO: 41) to P and mutating an amino acid residue P of the wild-type rice EPSPS corresponding to a site 101 (this site is corresponding to a site 116 of the wild-type rice EPSPS) of the *E. coli* EPSPS to S.

Figure 11:
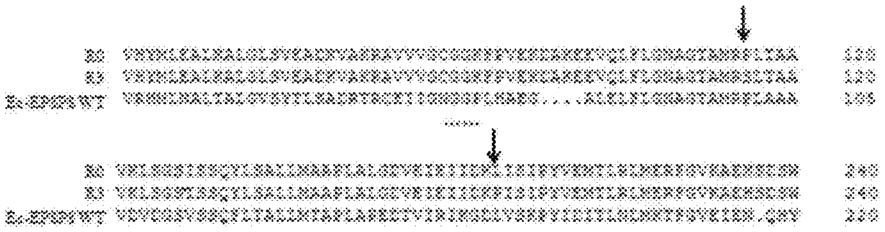
FIG. 11 shows partial alignment results of amino acid sequences of the three, namely, rice EPSPS mutant R3 (SEQ ID NO: 34), wild-type rice EPSPS (SEQ ID NO: 28) and *E. coli* EPSPS (SEQ ID NO: 41) provided in Example 11 of the present disclosure.

The amino acid sequences of the three, namely, the rice EPSPS mutant R3, the wild-type rice EPSPS and the *E. coli* EPSPS, are aligned as shown in FIG. 11, wherein a position indicated by an arrow is a mutation site, and Ec-EPSPS WT represents the *E. coli* EPSPS.

Besides, the present example further provides a nucleic acid molecule encoding the rice EPSPS mutant R3, which has a base sequence represented by SEQ ID NO: 33.

The rice EPSPS mutant R3 and the nucleic acid molecule encoding the rice EPSPS mutant R3 provided in the present example both can be obtained through a chemical synthesis method.

Example 12

A rice EPSPS mutant provided in the present example, named as R4, has an amino acid sequence represented by SEQ ID NO: 36.

The rice EPSPS mutant R4 provided in the present example can be obtained by mutating an amino acid residue S of a wild-type rice EPSPS (named as R0, with an amino acid sequence represented by SEQ ID NO: 28) corresponding to a site 247 (this site is corresponding to a site 267 of the wild-type rice EPSPS) of an *E. coli* EPSPS (with an amino acid sequence represented by SEQ ID NO: 41) to G.

Figure 12:
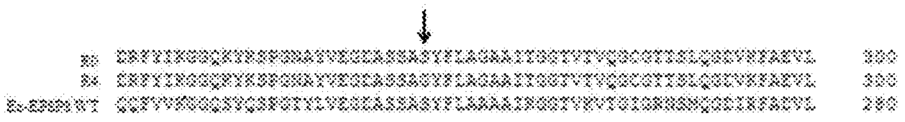
FIG. 12 shows partial alignment results of amino acid sequences of the three, namely, rice EPSPS mutant R4 (SEQ ID NO: 36), wild-type rice EPSPS (SEQ ID NO: 28) and *E. coli* EPSPS (SEQ ID NO: 41) provided in Example 12 of the present disclosure.

The amino acid sequences of the three, namely, the rice EPSPS mutant R4, the wild-type rice EPSPS and the *E. coli* EPSPS, are aligned as shown in FIG. 12, wherein a position indicated by an arrow is a mutation site, and Ec-EPSPS WT represents the *E. coli* EPSPS.

Besides, the present example further provides a nucleic acid molecule encoding the rice EPSPS mutant R4, which has a base sequence represented by SEQ ID NO: 35.

The rice EPSPS mutant R4 and the nucleic acid molecule encoding the rice EPSPS mutant R4 provided in the present example both can be obtained through a chemical synthesis method.

Example 13

A rice EPSPS mutant provided in the present example, named as R5, has an amino acid sequence represented by SEQ ID NO: 38.

The rice EPSPS mutant R5 provided in the present example can be obtained by mutating an amino acid residue S of a wild-type rice EPSPS (named as R0, with an amino acid sequence represented by SEQ ID NO: 28) corresponding to a site 247 (this site is corresponding to a site 267 of the wild-type rice EPSPS) of an *E. coli* EPSPS (with an amino acid sequence represented by SEQ ID NO: 41) to G and mutating an amino acid residue P of the wild-type rice EPSPS corresponding to a site 101 (this site is corresponding to a site 116 of the wild-type rice EPSPS) of the *E. coli* EPSPS to S.

Figure 13:
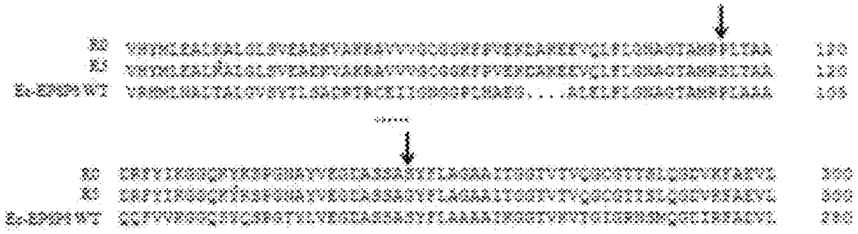
FIG. 13 shows partial alignment results of amino acid sequences of the three, namely, rice EPSPS mutant R5 (SEQ ID NO: 38), wild-type rice EPSPS (SEQ ID NO: 28) and *E. coli* EPSPS (SEQ ID NO: 41) provided in Example 13 of the present disclosure.

The amino acid sequences of the three, namely, the rice EPSPS mutant R5, the wild-type rice EPSPS and the *E. coli* EPSPS, are aligned as shown in FIG. 13, wherein a position indicated by an arrow is a mutation site, and Ec-EPSPS WT represents the *E. coli* EPSPS.

Besides, the present example further provides a nucleic acid molecule encoding the rice EPSPS mutant R5, which has a base sequence represented by SEQ ID NO: 37.

The rice EPSPS mutant R5 and the nucleic acid molecule encoding the rice EPSPS mutant R5 provided in the present example both can be obtained through a chemical synthesis method.

Example 14

A rice EPSPS mutant provided in the present example, named as R6, has an amino acid sequence represented by SEQ ID NO: 40.

The rice EPSPS mutant R6 provided in the present example can be obtained by mutating an amino acid residue S of a wild-type rice EPSPS (named as R0, with an amino acid sequence represented by SEQ ID NO: 28) corresponding to a site 247 (this site is corresponding to a site 267 of the wild-type rice EPSPS) of an *E. coli* EPSPS (with an amino acid sequence represented by SEQ ID NO: 41) to G, mutating an amino acid residue P of the wild-type rice EPSPS corresponding to a site 101 (this site is corresponding to a site 116 of the wild-type rice EPSPS) of the *E. coli* EPSPS to S and mutating an amino acid residue L of the wild-type rice EPSPS corresponding to a site 195 (this site is corresponding to a site 214 of the wild-type rice EPSPS) of the *E. coli* EPSPS to P.

Figure 14:
FIG. 14 shows partial alignment results of amino acid sequences of the three, namely, rice EPSPS mutant R6 (SEQ ID NO: 40), wild-type rice EPSPS (SEQ ID NO: 28) and *E. coli* EPSPS (SEQ ID NO: 41) provided in Example 14 of the present disclosure.

The amino acid sequences of the three, namely, the rice EPSPS mutant R6, the wild-type rice EPSPS and the *E. coli* EPSPS, are aligned as shown in FIG. 14, wherein a position indicated by an arrow is a mutation site, and Ec-EPSPS WT represents the *E. coli* EPSPS.

Besides, the present example further provides a nucleic acid molecule encoding the rice EPSPS mutant R6, which has a base sequence represented SEQ ID NO: 39.

The rice EPSPS mutant R6 and the nucleic acid molecule encoding the rice EPSPS mutant R6 provided in the present example both can be obtained through a chemical synthesis method.

Experiment Example 1

Figure 15:
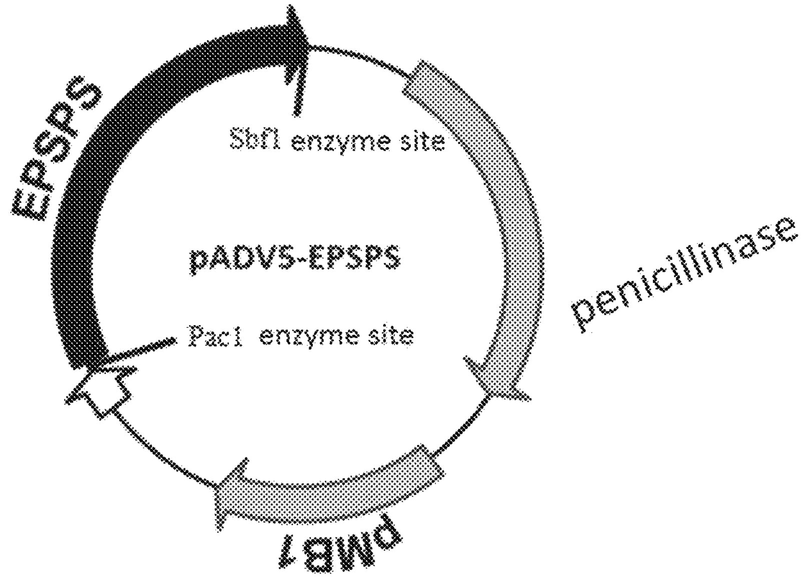
FIG. 15 is a schematic structural diagram of a pADV5 vector provided in Experiment Example 1 of the present disclosure.

A method for detecting the glyphosate resistance of the soybean EPSPS mutant G1 provided in Example 1 and the soybean EPSPS mutant G3 provided in Example 2 is as follows:

according to the sequence of the nucleic acid molecule provided in the example, synthesizing the encoding gene that encodes the soybean EPSPS mutant G1 or G3 using a chemical synthesis method, introducing enzyme sites (Pac1 and Sbf1) at two ends thereof, connecting to an expression vector (for example, a pADV5 vector, the structure of which is as shown in FIG. 15) that has undergone the same restriction enzyme digestion treatment under the action of ligase after restriction enzyme digestion, then transforming double knockout *E. coli*, picking positive colonies after verification, inoculating the positive colonies to M9 culture media containing different glyphosate concentrations for growth, and observing the growth situation of the *E. coli*.

Figure 16:
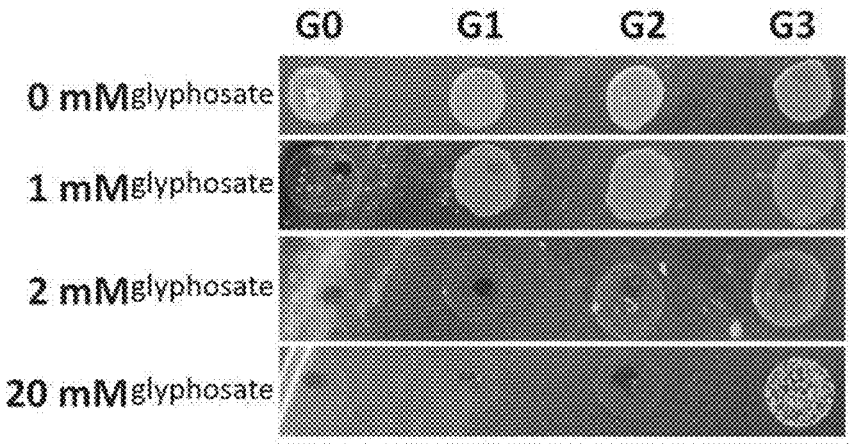
FIG. 16 shows growth results of *E. coli* transformed by the soybean EPSPS mutant G1 provided in Example 1 and the soybean EPSPS mutant G3 provided in Example 2, provided in Experiment Example 1 of the present disclosure, in culture media containing different glyphosate concentrations.

The wild-type soybean EPSPS (with an amino acid sequence represented by SEQ ID NO: 2 and an encoding gene sequence represented by SEQ ID NO: 1) and the soybean EPSPS mutant G2 (with an amino acid sequence represented by SEQ ID NO: 6, and a corresponding encoding gene sequence represented by SEQ ID NO: 5) merely containing the mutation P114(101)S were taken as controls. Results are as shown in FIG. 16.

In the above, the M9 basal culture medium can be prepared by the following method:

5×M9 salt solution: 6.78 g of $Na_2HPO_4$, 3.0 g of $KH_2PO_4$, 0.5 g of NaCl, and 1.0 g of $NH_4Cl$ were weighed, added with $ddH_2O$ to 200 ml, and subjected to high-temperature and high-pressure sterilization treatment;

20% glucose: 20 g of glucose was weighed, added with 80 ml of $ddH_2O$ for dissolving, diluted to 100 ml, and subjected to filtration and sterilization treatment;

1.0 M $MgSO_4$: 24.6 g of $MgSO_4$-$7H_2O$ was weighed, dissolved with 80 ml of $ddH_2O$, diluted to 100 ml, and subjected to sterilization treatment;

1.0 M $CaCl_2$: 11.1 g of $CaCl_2$ was weighed, dissolved with 80 ml of $ddH_2O$, diluted to 100 ml, and subjected to sterilization treatment; and 1000 ml of the M9 basal culture media were prepared by adding $ddH_2O$ to 200 ml of 5×M9 salt solution, 20 ml of 20% glucose, 2 ml of 1.0 M $MgSO_4$ and 0.1 ml of 1.0 M $CaCl_2$ to make up to 1000 ml.

In the above, the *E. coli* used was double knockout *E. coli*, namely, EPSPS defective *E. coli* (*E. coli* DH5α with EPSPS gene and C-P Lyase gene being knocked out, named as EDCE, wherein for a preparation method thereof, reference can be made to a Chinese invention patent with the filing number CN2016103256926).

It can be seen from the results of FIG. 16 that:

In the culture media containing 0 mM glyphosate, all of the defective *E. coli* transformed by the encoding genes that encode the wild-type soybean EPSPS G0 and the soybean EPSPS mutant G1/G2/G3 could grow, indicating that the EPSPS encoded by the four sequences had normal EPSPS enzyme activity;

In the culture media containing 1 mM glyphosate, the *E. coli* transformed by the wild-type soybean EPSPS G0 substantially could not grow, but the growth of the *E. coli* transformed by the soybean EPSPS mutant G1 was obviously superior to that of the *E. coli* transformed by G0, indicating that the single mutant containing L212(195)P had the glyphosate resistance obviously superior to that of the wild type; and The *E. coli* transformed by the soybean EPSPS mutant G2 and the soybean EPSPS mutant G3 both could grow in the culture media containing 20 mM glyphosate, but the growth of the *E. coli* transformed by the soybean EPSPS mutant G3 was superior to that of the *E. coli* transformed by the soybean EPSPS mutant G2, indicating that the site mutation L212(195)P could further improve the glyphosate resistance on the basis of the glyphosate resistance provided by the site mutation P114(101)S.

Experiment Example 2

The glyphosate resistance of the soybean EPSPS mutant G4 provided in Example 3 and the soybean EPSPS mutant G5 provided in Example 4 was verified with reference to the detection method in Experiment Example 1. Results are as shown in FIG. 17.

Figure 17:
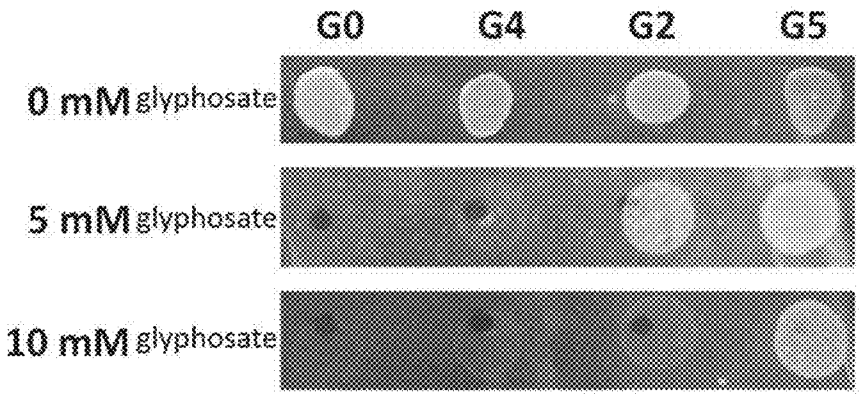
FIG. 17 shows growth results of *E. coli* transformed by the soybean EPSPS mutant G4 provided in Example 3 and the soybean EPSPS mutant G5 provided in Example 4, provided in Experiment Example 2 of the present disclosure, in culture media containing different glyphosate concentrations.

It can be seen from the results of FIG. 17 that:

In the culture media containing 0 mM glyphosate, all of the defective *E. coli* transformed by the encoding genes that encode the wild-type soybean EPSPS G0 and the soybean EPSPS mutant G4/G2/G5 could grow;

In the culture media containing 5 mM glyphosate, the *E. coli* transformed by the wild-type soybean EPSPS G0 substantially could not grow, but the growth of *E. coli* transformed by G4 was superior to that of the *E. coli* transformed by G0, indicating that the glyphosate resistance of the EPSPS containing a single mutation S265(247)G was superior to that of the wild-type EPSPS; and The *E. coli* transformed by the soybean EPSPS mutant G2 and transformed by the soybean EPSPS mutant G5 both could grow in the culture media containing 10 mM glyphosate, but the growth of the *E. coli* transformed by G5 was obviously superior to that of the *E. coli* transformed by G2, indicating that the mutation S265(247)G could further substantially improve the glyphosate resistance on the basis of the glyphosate resistance provided by the mutation P114 (101)S.

Experiment Example 3

The wild-type wheat EPSPS (with an amino acid sequence represented by SEQ ID NO: 14, and a corresponding encoding gene sequence represented by SEQ ID NO: 13) and the wheat EPSPS mutant T2 (with an amino acid sequence represented by SEQ ID NO: 18, and a corresponding encoding gene sequence represented by SEQ ID NO: 17) merely containing the mutation P118(101)S were taken as controls to verify the glyphosate resistance of the wheat EPSPS mutants T1 and T3 provided in Example 5 and Example 6, and reference can be made to Experiment Example 1 for the method. Results are as shown in FIG. 18.

Figure 18:
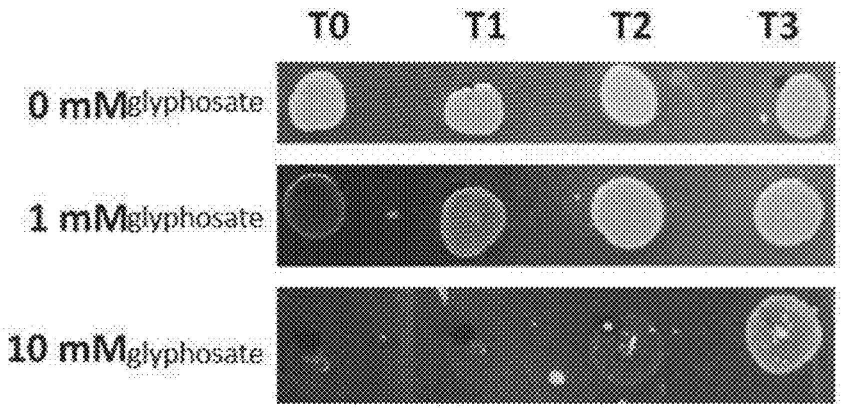
FIG. 18 shows growth results of *E. coli* transformed by the wheat EPSPS mutant T1 provided in Example 5 and the wheat EPSPS mutant T3 provided in Example 6, provided in Experiment Example 3 of the present disclosure, in culture media containing different glyphosate concentrations.

It can be seen from the results of FIG. 18 that:

In the culture media containing 0 mM glyphosate, all of the defective *E. coli* transformed by the wild-type wheat EPSPS T0 and the wheat EPSPS mutant T1/T2/T3 could grow;

In the culture media containing 1 mM glyphosate, the *E. coli* transformed by the wild-type T0 substantially could not grow, but the growth of the *E. coli* transformed by T1 was obviously superior to that of the *E. coli* transformed by T0, indicating that the single-mutation wheat EPSPS containing S269(247)G had the glyphosate resistance obviously superior to that of the wild-type wheat EPSPS; and The *E. coli* transformed by T2 and T3 both could grow in the culture media containing 10 mM glyphosate, but the growth of *E. coli* transformed by T3 was obviously superior to that of the *E. coli* transformed by T2, indicating that the mutation S269(247)G could further substantially improve the glyphosate resistance on the basis of the glyphosate resistance provided by the mutation P118(101)S.

It is thus indicated that the wheat EPSPS mutants T1 and T3 provided in Example 5 and Example 6 have glyphosate resistance.

Experiment Example 4

A method for verifying the glyphosate resistance of the wheat EPSPS mutants T4, T5, and T6 provided in Examples 7-9 is the same as that in Experiment Example 3. Results are as shown in FIG. 19.

Figure 19:
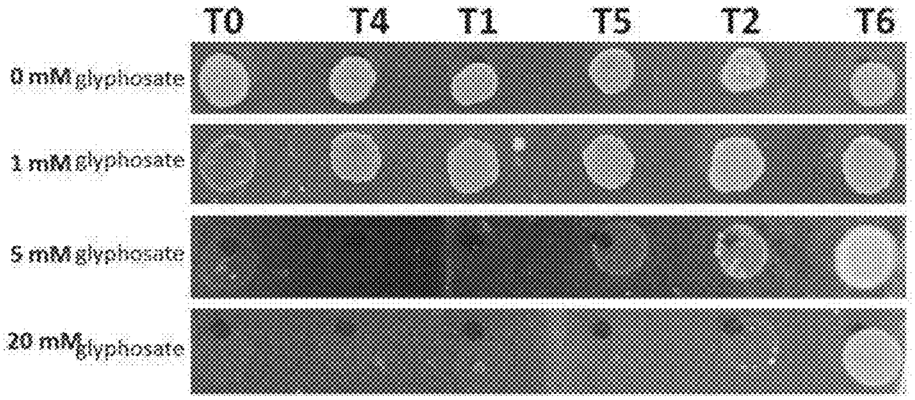
FIG. 19 shows growth results of *E. coli* transformed by the wheat EPSPS mutants T4, T5, and T6 provided in Examples 7-9, provided in Experiment Example 4 of the present disclosure, in culture media containing different glyphosate concentrations.

It can be seen from the results of FIG. 19 that:

In the culture media containing 0 mM glyphosate, all of the defective *E. coli* transformed by the wild-type wheat EPSPS T0 and the wheat EPSPS mutants T1, T2, T3, T4, T5, and T6 could grow, indicating that the wheat mutants T4, T5, and T6 also had normal EPSPS enzyme activity;

In the culture media containing 1 mM glyphosate, the *E. coli* transformed by the wild-type wheat EPSPS T0 substantially could not grow, but all the *E. coli* transformed by other mutants (T1, T2, T3, T4, T5, and T6) could grow normally, indicating that the glyphosate resistance of these single mutants was obviously superior to that of the wild type; and In the culture media containing 5 mM glyphosate, the *E. coli* transformed by T1 and T4 did not grow obviously, but the *E. coli* transformed by T5 grew obviously, indicating that the glyphosate resistance endowed by the mutations L216(195)P and S269(247)G could be superposed, and then the glyphosate resistance is improved.

The *E. coli* transformed by T2 and T6 could grow in the culture media containing 5 mM and 20 mM glyphosate, but the growth of the *E. coli* transformed by T6 was obviously superior to that of the *E. coli* transformed by T2, indicating that double mutations L216(195)P and S269(247)G could further substantially improve the glyphosate resistance on the basis of the glyphosate resistance provided by the mutation P118(101)S.

Experiment Example 5

The wild-type rice EPSPS R0 (with an amino acid sequence represented by SEQ ID NO: 28, and a corresponding encoding gene sequence represented by SEQ ID NO: 27) and the rice EPSPS mutant R2 (with an amino acid sequence represented by SEQ ID NO: 32, and a corresponding encoding gene sequence represented by SEQ ID NO: 31) merely containing the mutation P116(101)S were taken as controls to verify the glyphosate resistance of the rice EPSPS mutants R1 and R3 provided in Examples 10 and 11, and reference can be made to Experiment Example 1 for the method. Results are as shown in FIG. 20.

Figure 20:
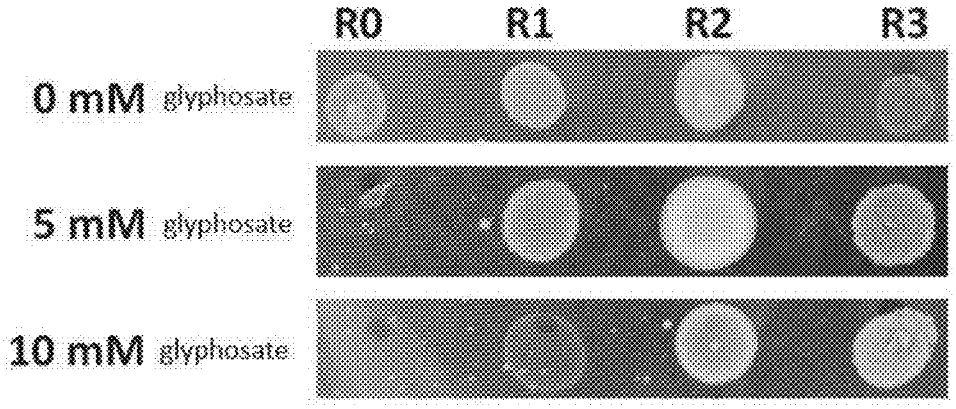
FIG. 20 shows growth results of *E. coli* transformed by the rice EPSPS mutants R1 and R3 provided in Examples 10 and 11, provided in Experiment Example 5 of the present disclosure, in culture media containing different glyphosate concentrations.

It can be seen from the results of FIG. 20 that:

In the culture media containing 0 mM glyphosate, all of the defective *E. coli* transformed by the wild-type rice EPSPS R0 and the rice EPSPS mutants R1, R2, and R3 could grow, indicating that the rice mutants R1, R2, and R3 also had normal EPSPS enzyme activity;

In the culture media containing 5 mM glyphosate, the *E. coli* transformed by the wild-type R0 could not grow, but the *E. coli* transformed by R1 could grow normally, and the *E. coli* transformed by R1 also grew obviously in the culture media containing 10 mM glyphosate, indicating that the single-mutation rice EPSPS mutant containing L214(195)P had the glyphosate resistance obviously superior to that of the wild type; and The *E. coli* transformed by R2 and R3 both could grow in the culture media containing 10 mM glyphosate, but the growth of the *E. coli* transformed by R3 was superior to that of the *E. coli* transformed by R2, indicating that the mutation L214(195)P could further improve the glyphosate resistance on the basis of the glyphosate resistance provided by the mutation P116(101)S.

It is thus indicated that the mutation L214(195)P could endow the rice EPSPS mutant with the glyphosate resistance.

Experiment Example 6

A method for verifying the glyphosate resistance of the rice EPSPS mutants R4 and R5 provided in Examples 12 and 13 is the same as that in Experiment Example 5. Results are as shown in FIG. 21.

Figure 21:
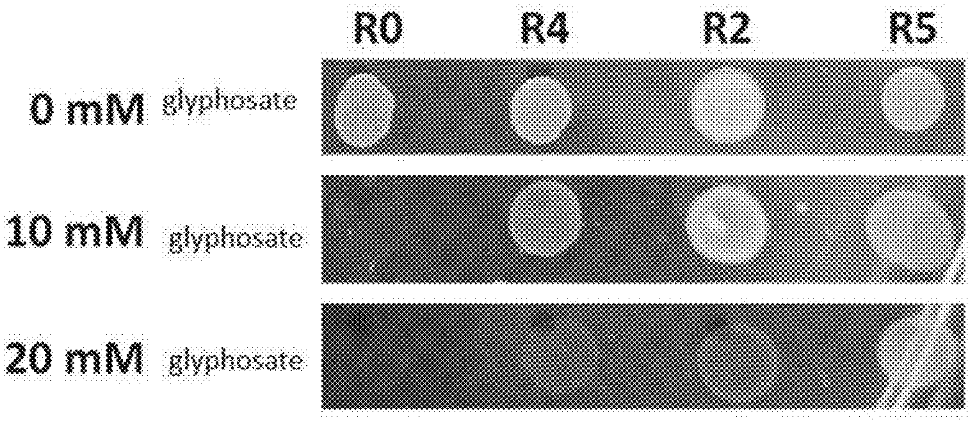
FIG. 21 shows growth results of *E. coli* transformed by the rice EPSPS mutants R4 and R5 provided in Examples 12 and 13, provided in Experiment Example 6 of the present disclosure, in culture media containing different glyphosate concentrations.

It can be seen from the results of FIG. 21 that:

In the culture media containing 0 mM glyphosate, all of the defective *E. coli* transformed by the wild-type rice EPSPS R0 and the rice EPSPS mutants R4, R2, and R5 could grow, indicating that the rice mutants R4 and R5 also had normal EPSPS enzyme activity;

In the culture media containing 10 mM glyphosate, the *E. coli* transformed by the wild-type R0 could not grow, but the *E. coli* transformed by R4 could grow normally, and the *E. coli* transformed by R4 also grew obviously in the culture media containing 20 mM glyphosate, indicating that the single-mutation EPSPS mutant containing S267(247)G had the glyphosate resistance obviously superior to that of the wild type; and The *E. coli* transformed by R2 and R5 both could grow in the culture media containing 20 mM glyphosate, but the growth of the *E. coli* transformed by R5 was obviously superior to that of the *E. coli* transformed by R2, indicating that the mutation S267(247)G could further substantially improve the glyphosate resistance on the basis of the glyphosate resistance provided by the mutation P116(101)S.

It is thus indicated that the mutation S267(247)G could endow the rice EPSPS mutant with the glyphosate resistance or enhance the glyphosate resistance of the rice EPSPS mutant.

Experiment Example 7

A method for verifying the glyphosate resistance of the rice EPSPS mutant R6 provided in Example 14 is the same as that in Experiment Example 5. Results are as shown in FIG. 22.

Figure 22:
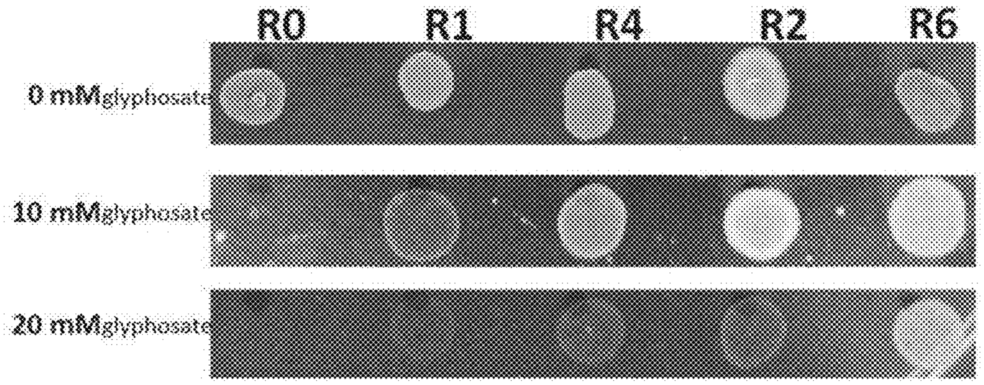
FIG. 22 shows growth results of *E. coli* transformed by the rice EPSPS mutant R6 provided in Example 14, provided in Experiment Example 7 of the present disclosure, in culture media containing different glyphosate concentrations.

It can be seen from the results of FIG. 22 that:

In the culture media containing 0 mM glyphosate, all of the defective *E. coli* transformed by the wild-type rice EPSPS R0 and the rice EPSPS mutants R1, R4, R2, and R6 could grow, indicating that the rice mutants R6 also had normal EPSPS enzyme activity;

In the culture media containing 10 mM glyphosate, the *E. coli* transformed by the wild-type R0 could not grow, but the *E. coli* transformed by R1 and R4 could grow normally, and the *E. coli* transformed by R1 also grew obviously in the culture media containing 20 mM glyphosate, indicating that the single-mutation rice EPSPS mutant containing L214(195)P had the glyphosate resistance obviously superior to that of the wild type, meanwhile, the growth of the *E. coli* transformed by R4 was superior to that of the *E. coli* transformed by R1 in the culture media containing 10 mM glyphosate, indicating that the glyphosate resistance of the S267(247)G mutation was stronger than L214(195)P;

The *E. coli* transformed by R2 and R6 both could grow in the culture media containing 20 mM glyphosate, but the growth of the *E. coli* transformed by R6 was superior to that of the *E. coli* transformed by R2, indicating that simultaneously containing the two mutations L214(195)P and S267(247)G could further improve the glyphosate resistance on the basis of the glyphosate resistance provided by the mutation P116(101)S.

The above indicates that the two mutations L214(195)P and S267(247)G could further improve the glyphosate resistance of the rice EPSPS mutant on the basis of the glyphosate resistance provided by the mutation P116(101)S.

The above results sufficiently indicate that compared with the *E. coli* EPSPS sequence, the amino acid sequence of the plant EPSPS mutant containing the mutation L195P corresponding to the site 195 of the *E. coli* EPSPS and/or containing the mutation S247G corresponding to the site 247 of the *E. coli* EPSPS can endow the plant EPSPS mutant with the glyphosate resistance or improve the glyphosate resistance of the plant EPSPS mutant.

Experiment Example 8

Figure 23:
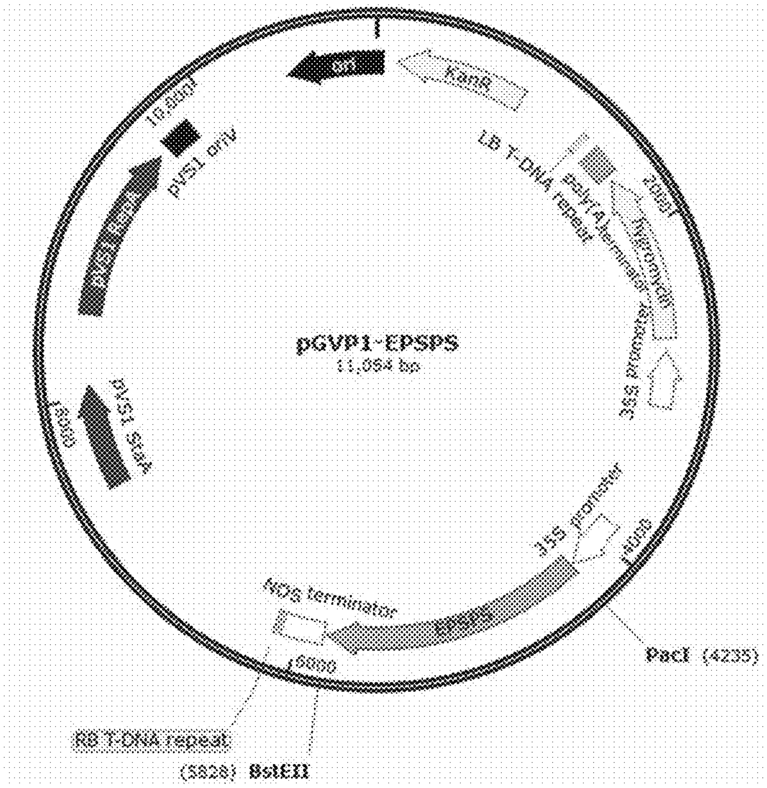
FIG. 23 is a schematic structural diagram of a pGVP1-EPSPS vector provided in Experiment Example 8 of the present disclosure.

A method for detecting the glyphosate resistance of G1 (SEQ ID NO: 4) provided in Example 1, G3 (SEQ ID NO: 8) provided in Example 2, G4 (SEQ ID NO: 10) provided in Example 3, the soybean EPSPS mutant G5 (SEQ ID NO: 12) provided in Example 4, T1 (SEQ ID NO: 16) provided in Example 5, T3 (SEQ ID NO: 20) provided in Example 6, T4 (SEQ ID NO: 22) provided in Example 7, T5 (SEQ ID NO: 24) provided in Example 8, the wheat EPSPS mutant T6 (SEQ ID NO: 26) provided in Example 9, R1 (SEQ ID NO: 30) provided in Example 10, R3 (SEQ ID NO: 34) provided in Example 11, R4 (SEQ ID NO: 36) provided in Example 12, R5 (SEQ ID NO: 38) provided in Example 13, and the rice EPSPS mutant R6 (SEQ ID NO: 40) provided in Example 14 in the transgenic rice is as follows:

The plasmids (containing the EPSPS mutation gene) of the monoclonal resistant bacteria of pADV5-EPSPS in Examples 1-7 were extracted by a conventional method, followed by double enzyme digestion by Pac1 and BstEII, the small fragments were collected, and then the small fragments were ligated by using T4 DNA ligase, to the pGVP1 vectors that had undergone the same double enzyme digestion, to obtain a pGVP1-EPSPS vector having a structure as shown in FIG. 23.

EHA105 (*Agrobacterium tumefaciens*) competent cells were transformed by the pGVP1-EPSPS vector, and single colonies were picked up to perform bacterial colony PCR detection to identify positive strains; then the positive strains were inoculated into 1 mL of YEP culture medium containing 50 $\mu g \cdot mL^{-1}$ kanamycin and 50 $\mu g \cdot mL^{-1}$ rifampin to propagate, and then preserved at −80° C., or used for subsequent experiment.

Rice transformation:

400 μl of bacterium containing the target gene vector preserved at −80° C. was added to a culture dish of solid culture media containing YEP+50 μg/mL rifampin+50 μg/mL kanamycin, and cultured in the dark at 28° C. for 24 hours, then this bacterium was added to an infection culture medium, and this bacterial solution was adjusted to OD=0.2 as an infection liquid.

Sterilization and pre-culturing: mature rice (Nipponbare) seeds were manually shelled, and full seeds without bacterial plaque were selected, and sterilized according to following steps: putting the seeds into a 50 ml sterile centrifuge tube, adding 70% alcohol for disinfection for 30 seconds, pouring out the alcohol, and cleaning the seeds once with sterile water; adding 10-20 ml of 2.6% sodium hypochlorite solution for soaking and sterilizing for 20 minutes, pouring out the sodium hypochlorite solution, and soaking and cleaning the seeds with sterile water for 6-7 times, 3 minutes each time.

Induction and subculturing: the seeds were put on sterile filter paper for drying, and mature embryos were put in an induction culture medium with 12 embryos in each dish; the culture dishes were sealed with a sealing film after the operation was finished, the mature embryos were cultured in the dark at 30° C. for 21-28 days, calluses were transferred into a fresh culture medium, and continuously cultured for about 7-14 days, and spherical calluses with a size of 1-2 mm were taken as infection receptors.

Infection and co-culturing:

the calluses were inoculated into a centrifuge tube or a culture cup, the prepared *Agrobacterium tumefaciens* suspension liquid was added for infection for 10 minutes, wherein the calluses were shaken several times; the bacterial solution was poured out, the calluses were taken out, and placed on sterile filter paper to suck out the surface bacterial solution (about 30 minutes); and the calluses were put on sterile filter paper in a culture dish, and cultured in the dark at 25° C. for 2-3 days.

Recovery culturing: the calluses having undergone co-culturing were inoculated in a recovery culture medium, and cultured in the dark at 30° C. for 5-7 days. First round of screening: the calluses were transferred to screening culture media 1 (S1) and cultured in the dark at 30° C. for 14 days.

Second round of screening: the calluses were then transferred to screening culture media 2 (S2) and cultured in the dark at 30° C. for 14 days.

First round of differentiation: the screened resistant calluses were transferred into differentiation culture medium, illuminated in light at 30° C. for 19 hours, and cultured for about 21 days. Second round of differentiation: newborn young buds were picked out and transferred to a new differentiation culture medium, and continuously cultured for about 21 days.

When growing to about 2 cm, newborn seedlings were transferred to a rooting culture medium to be cultured in light (16/8 h) at 30° C. for 3~4 weeks, after roots were induced and the seedlings grew to 7~10 cm, the seedlings were taken out from the culture medium, to wash off the culture medium contaminated on the roots, and the seedlings were transplanted to a growing tray, and continuously cultured for about 10 d, and then transferred to greenhouse or field.

Formula of the culture media:

Induction culture medium: NB BasaL Medium [N6 macronutrients+MS iron salt solution+B5 micronutrients and organic nutrients]+hydrolyzing casein 0.3 g/L+L-proline 2.787 g/L+sucrose 30 g/L+2,4-D 4 mg/L+agar 8 g/L, pH5.8.

Infection culture medium: NB BasaL Medium [N6 macronutrients+MS iron salt solution+B5 micronutrients and organic nutrients]+L-proline 0.7 g/L+sucrose 68.4 g/L+glucose 36 g/L+2,4-D 2 mg/L pH5.2 (in small pot at 115° C.), AS 20 mg/L added when in use.

Co-culturing culture medium: NB BasaL Medium [N6 macronutrients+MS iron salt solution+B5 micronutrients and organic nutrients]+hydrolyzing casein 0.3 g/L+L-proline 2.787 g/L+sucrose 30 g/L+2,4-D 1 mg/L pH5.2, AS 20 mg/L added when in use.

Recovery culture medium: NB BasaL Medium [N6 macronutrients+MS iron salt solution+B5 micronutrients and organic nutrients]+glutamine 0.2 g/L+L-proline 2.787 g/L+sucrose 30 g/L+2,4-D 4 mg/L+agar 8 g/L, pH5.8. Cefotaxime (100 mg/L)+Timentin 100 mg/L+Vancomycin 50 mg/L were added after sterilization.

Screening culture medium 1 (S1): NB BasaL Medium [N6 macronutrients+MS iron salt solution+B5 micronutrients and organic nutrients]+glutamine 0.2 g/L+L-proline 2.787 g/L+sucrose 30 g/L+2,4-D 2 mg/L+agar 8 g/L, pH5.8. Cefotaxime 100 mg/L+Timentin 100 mg/L+Vancomycin 50 mg/L were added after sterilization. Selective agent (Glyphosate 400 mg/L, or hygromycin 50 mg/L) was added.

Screening culture medium 2 (S2): NB BasaL Medium [N6 macronutrients+MS iron salt solution+B5 micronutrients and organic nutrients]+glutamine 0.2 g/L+L-proline 2.787 g/L+sucrose 30 g/L+2,4-D 2 mg/L+agar 8 g/L, pH5.8.

Cefotaxime 100 mg/L+Timentin 100 mg/L+Vancomycin 50 mg/L were added after sterilization. Selective agent (Glyphosate 50-400 mg/L, or hygromycin 30 mg/L) was added.

Differentiation culture medium (F): MS BasaL Medium [MS macronutrients+iron salt solution+micronutrients and organic nutrients]+glutamine 0.2 g/L+sucrose 30 g/L+sorbitol 30 g/L+agar 8 g/L pH5.8. Cefotaxime 200 mg/L+KT 2 mg/L+NAA 0.02 mg/L+GLyphosate 1-5 mg/L were added after sterilization.

Selective agent (Glyphosate 1-5 mg/L, or hygromycin 20 mg/L was added.

Rooting culture medium: ½ MS BasaL Medium [MS macronutrients+iron salt solution+micronutrients and organic nutrients]+inositol 0.1 g/L+sucrose 30 g/L+agar 8 g/L, pH5.8. Cefotaxime 100 mg/L and NAA 0.2 mg/L were added after sterilization.

Detection of transgenic plants:

The rice plants transformed by the EPSPS mutant gene were detected using the PCR method, and forward and reverse detecting primers were designed according to the pGVP1-EPSPS vector sequence and the rice reference gene, and primer sequences are as follows:

For parts of sequences of the vector:

```
CaMV15:
                                        (SEQ ID NO: 42)
5'-GGTGGCTCCTACAAATGCCATC-3';

CTS3:
                                        (SEQ ID NO: 43)
5'-GAGCCAATTAACGTCATCCCAC-3';

an amplified fragment had a size of 452 bp;
For the rice reference gene:
OsF:
                                        (SEQ ID NO: 44)
5'-GCTTCTGACCAGCCCATTATTCTGC-3';

OsR:
                                        (SEQ ID NO: 45)
5'-CCCTCAAGGGTAAGCTCATCTCTCTTC-3';

an amplified fragment had a size of 629 bp.
```

Genomic DNAs of the rice plants transformed by the pGVP1-EPSPS gene were extracted, respectively, and homogenized to 100 ng/μL.

A PCR detection system: 10 μL 2xTsINGKe, 2 μL of a primer mixture (10 μmol/L of OsF, OsR, CaMV15, CTS3, 0.5 μL for each), 1 μL of genomic DNA template (100 ng/μL), 7 μL of $ddH_2O$.

A PCR detection procedure: 94° C., 3 min; 94° C., 30 s; 62° C., 30 s; 72° C., 45 s; 30 cycles; 72° C., 10 min; maintained at 12° C.

PCR amplification products underwent 1.5% agarose gel electrophoresis, wherein products having bands at site 452 bp and site 629 bp were transgenic positive rice plants.

In the present example, the glyphosate resistance of the EPSPS mutant in transgenic rice plants was verified. An experiment method is as follows:

The transgenic rice seedlings transplanted were uniformly arranged in a same experiment area (preventing leaves from overlapping). The areas occupied by the experiment groups and the control group were calculated, and according to the areas, glyphosate was sprayed at a 1× dosage of 1060 g/hectare (0.106 g/$m^2$). 2× dosage was 2120 g/hectare, 5× dosage was 5300 g/hectare, and 20× dosage was 21200 g/hectare.

Commercially available Roundup® 41% ammonium glyphosate was used. Roundup® ammonium glyphosate with corresponding volumes was taken according to the above sprayed concentrations, then diluted with 20 times of volume of water, and then uniformly sprayed on the plants in the experiment groups and the control group. After leaf surfaces were dry, the plants were moved into greenhouse or outdoor to cultivate.

Statistical standards used to evaluate glyphosate resistance were as follows: if a plant was not damaged by glyphosate at all and grew normally, it was considered as a plant with high glyphosate resistance, denoted by "+++"; if a plant showed leaves yellowed to some extent and grew slightly slowly, it was considered as a plant with medium glyphosate resistance, denoted by "++"; if a plant had some leaves withered and grew quite slowly, it was considered as a plant with low glyphosate resistance, denoted by "+"; if a plant withered and died, it was considered as a plant with no glyphosate resistance (having no glyphosate resistance), denoted by "–" (Table 1).

After the glyphosate was sprayed at the 1× dosage, growth states of the plants in each group were observed and recorded on a $10^{th}$ day, and glyphosate was sprayed to the survived plants at the 2× dosage. The growth states of the plants in each group were observed and recorded 10 days later, and glyphosate was sprayed to the survived plants at the 5× dosage. The growth states of the plants in each group were observed and recorded 10 days later, and glyphosate was sprayed to the survived plants at the 20× dosage. The growth states of the plants in each group were observed and recorded 10 days later, and results are shown in Table 1, wherein corresponding numbers of plants denoted by –, +, ++ and +++ are listed, and "%++&+++" is percentage of plant having medium and high glyphosate resistance to the total number of plants observed.

TABLE 1

| | Resistance | G0 | G1 | G2 | G3 | G4 | G5 | T0 | T1 | T2 | T3 | T4 | T5 | T6 |
|---|---|---|---|---|---|---|---|---|---|---|---|---|---|---|
| 1× | – | 36 | 10 | 3 | 7 | 13 | 16 | 32 | 18 | 12 | 18 | 7 | 6 | 4 |
| dosage | + | 0 | 20 | 6 | 25 | 23 | 14 | 1 | 28 | 13 | 27 | 30 | 6 | 7 |
| | ++ | 0 | 4 | 5 | 37 | 9 | 18 | 0 | 15 | 15 | 33 | 18 | 3 | 15 |
| | +++ | 0 | 2 | 3 | 7 | 4 | 49 | 0 | 2 | 13 | 77 | 8 | 7 | 52 |
| | %++&+++ | 0.0 | 16.7 | 47.1 | 57.9 | 26.5 | 69.1 | 0.0 | 27.0 | 52.8 | 71.0 | 35.6 | 45.5 | 85.9 |
| 2× | – | 36 | 17 | 17 | 10 | 25 | 21 | 33 | 30 | 23 | 29 | 34 | 10 | 8 |
| dosage | + | 0 | 19 | 0 | 66 | 25 | 43 | 0 | 32 | 26 | 47 | 40 | 8 | 4 |
| | ++ | 0 | 0 | 0 | 0 | 01 | 23 | 0 | 1 | 3 | 46 | 0 | 4 | 25 |
| | +++ | 0 | 0 | 0 | 0 | 0 | 10 | 0 | 0 | 1 | 33 | 4 | 0 | 41 |
| | %++&+++ | 0.0 | 0.0 | 0.0 | 0.0 | 2.0 | 34.0 | 0.0 | 1.6 | 7.5 | 51.0 | 18.2 | 84.6 | 0.0 |
| 5× | – | 36 | 31 | 17 | 30 | 44 | 37 | 33 | 61 | 32 | 40 | 66 | 13 | 9 |
| dosage | + | 0 | 5 | 0 | 46 | 7 | 53 | 0 | 2 | 21 | 75 | 12 | 5 | 9 |
| | ++ | 0 | 0 | 0 | 0 | 0 | 6 | 0 | 0 | 0 | 38 | 0 | 4 | 37 |
| | +++ | 0 | 0 | 0 | 0 | 0 | 1 | 0 | 0 | 0 | 2 | 0 | 0 | 23 |

TABLE 1-continued

| | | | | | | | | | | | | | | |
|---|---|---|---|---|---|---|---|---|---|---|---|---|---|---|
| | &++&+++ | 0.0 | 0.0 | 0.0 | 0.0 | 0.0 | 7.2 | 0.0 | 0.0 | 0.0 | 25.8 | 0.0 | 18.2 | 76.9 |
| 20× | − | 36 | 36 | 17 | 68 | 51 | 73 | 33 | 63 | 42 | 93 | 78 | 16 | 15 |
| dosage | + | 0 | 0 | 0 | 8 | 0 | 24 | 0 | 0 | 11 | 57 | 0 | 3 | 7 |
| | ++ | 0 | 0 | 0 | 0 | 0 | 0 | 0 | 0 | 0 | 5 | 0 | 3 | 56 |
| | +++ | 0 | 0 | 0 | 0 | 0 | 0 | 0 | 0 | 0 | 0 | 0 | 0 | 0 |
| | &++&+++ | 0.0 | 0.0 | 0.0 | 0.0 | 0.0 | 0.0 | 0.0 | 0.0 | 0.0 | 3.2 | 0.0 | 13.6 | 71.8 |

| | Resistance | R0 | R1 | R2 | R3 | R4 | R5 | R6 |
|---|---|---|---|---|---|---|---|---|
| 1× | − | 30 | 6 | 2 | 1 | 7 | 3 | 2 |
| dosage | + | 1 | 1 | 9 | 18 | 46 | 0 | 7 |
| | ++ | 0 | 1 | 10 | 39 | 62 | 6 | 3 |
| | +++ | 0 | 11 | 37 | 24 | 44 | 10 | 18 |
| | %++&+++ | 0.0 | 63.2 | 81.0 | 76.8 | 66.7 | 84.2 | 70.0 |
| 2× | − | 31 | 10 | 9 | 1 | 11 | 6 | 8 |
| dosage | + | 0 | 3 | 17 | 59 | 136 | 3 | 3 |
| | ++ | 0 | 10 | 18 | 12 | 10 | 6 | 1 |
| | +++ | 0 | 1 | 14 | 10 | 2 | 4 | 18 |
| | %++&+++ | 45.8 | 55.2 | 26.8 | 7.5 | 52.6 | 63.3 | |
| 5× | − | 31 | 14 | 16 | 12 | 92 | 8 | 11 |
| dosage | + | 0 | 9 | 40 | 59 | 67 | 3 | 0 |
| | ++ | 0 | 1 | 2 | 11 | 0 | 8 | 6 |
| | +++ | 0 | 0 | 0 | 0 | 0 | 0 | 13 |
| | &++&+++ | 0.0 | 4.2 | 3.4 | 13.4 | 0.0 | 42.1 | 63.3 |
| 20× | − | 31 | 20 | 57 | 48 | 151 | 11 | 11 |
| dosage | + | 0 | 4 | 1 | 28 | 8 | 8 | 0 |
| | ++ | 0 | 0 | 0 | 6 | 0 | 0 | 11 |
| | +++ | 0 | 0 | 0 | 0 | 0 | 0 | 8 |
| | &++&+++ | 0.0 | 0.0 | 0.0 | 7.3 | 0.0 | 0.0 | 63.3 |

It can be seen from the results of Table 1 that:

after the glyphosate was sprayed at the 1× dosage, all the rice transformed by the wild-type soybean EPSPS G0 had no resistance and died, but the glyphosate resistance of the rice seedlings transformed by the soybean EPSPS mutants G1 and G4 were obviously superior to that of the rice seedlings transformed by G0, 16.7% of the rice seedlings transformed by G1 and 26.5% of the rice seedlings transformed by G4 had medium glyphosate resistance or high glyphosate resistance, and some of the transgenic rice seedlings transformed by G4 still survived under the 2× and 5× glyphosate dosages, indicating that the single mutant containing L212(195)P and the single mutant containing S265(247)G had the glyphosate resistant obviously superior to that of the wild type;

The rice transformed by the soybean EPSPS mutant G2, the soybean EPSPS mutant G3 and the soybean EPSPS mutant G5 had certain resistance to glyphosate at the 1× dosage, but for a plant with relative high glyphosate resistance, the proportion (57.9%) of the rice transformed by G3 and the proportion (69.1%) of the rice transformed by G5 were obviously higher than that of the rice transformed by G2 (47.1%), all rice seedlings containing the soybean EPSPS mutant G2 died at the 2× or higher dosage, and some of the rice seedlings containing the soybean EPSPS mutants G3 and G5 still survived under the 2×, 5× and 20× dosages, indicating that the site mutation L212(195)P and the site mutation S265(247)G both could substantially further improve the glyphosate resistance on the basis of the glyphosate resistance provided by the site mutation P114(101)S.

After the glyphosate was sprayed at the 1× dosage, all the rice transformed by the wild-type wheat EPSPS T0 had no resistance, one was seriously damaged, and all the others died, but the glyphosate resistance of the rice seedlings transformed by the wheat EPSPS mutants T4, T1 and T5 was obviously superior to that of the rice seedlings transformed by T0, 35.6% of the rice seedlings transformed by T4, 27.0% of the rice seedlings transformed by T1, and 45.5% of the rice seedlings transformed by T5 had medium glyphosate resistance or high glyphosate resistance, and some of the transgenic rice seedlings transformed by T4, T1 and T5 still survived under the 2× and 5× glyphosate dosages, indicating that the single mutant containing L216(195)P and the single mutant containing S269(247)G had the glyphosate resistant obviously superior to that of the wild type; and 13.6% of the transgenic rice seedlings transformed by T5 had medium glyphosate resistance under the 20× glyphosate dosage, indicating that the combined glyphosate resistant of the mutant containing L216(195)P and the mutant containing S269(247)G was superior to that of the single mutant, which gives superposed effect;

All the rice transformed by the wheat EPSPS mutant T2, the wheat EPSPS mutant T3 and the wheat EPSPS mutant T6 had relatively high resistance to glyphosate at the 1× dosage, but for a plant with relative high glyphosate resistance, the proportion (71.0%) of the rice transformed by T3 and the proportion (85.9%) of the rice transformed by T6 were obviously higher than the proportion (52.8%) of the rice transformed by T2, and at the 5× or higher dosage, none of the rice seedlings containing the wheat EPSPS mutant T2 achieved the level of medium glyphosate resistance, while 3.2% and 71.8% of the rice seedlings containing the wheat EPSPS mutants T3 and T6 had medium and high glyphosate resistance under the 20× dosage, indicating that the site mutation L216(195)P and the site mutation S269(247)G both could substantially further improve the glyphosate resistance on the basis of the glyphosate resistance provided by the site mutation P118(101)S.

After the glyphosate was sprayed at the 1× dosage, all the rice transformed by the wild-type rice EPSPS R0 had no resistance, one was seriously damaged, and all the others died, but the glyphosate resistance of the rice seedlings transformed by the rice EPSPS mutants R1 and R4 was obviously superior to that of the rice seedlings transformed by R0, 63.2% of the rice seedlings transformed by R1 and 66.7% of the rice seedlings transformed by R4 had medium or high glyphosate resistance, some of the transgenic rice seedlings transformed by R1 and R4 still survived at the 2×, 5× and even 20× glyphosate dosages, the proportions of the transgenic rice seedlings transformed by R1 and R4 having medium and high glyphosate resistance under the 2× glyphosate dosage were 45.8% and 7.5%, respectively, and even under the 5× glyphosate dosage, still 4.2% of the transgenic rice seedlings transformed by R1 had medium glyphosate resistance, indicating that the glyphosate resistant of the single mutant containing L214(195)P and the single mutant containing S267(247)G were obviously superior to that of the wild type;

All of the rice transformed by the rice EPSPS mutant R2, the rice EPSPS mutant R3, the rice EPSPS mutant R5 and the rice EPSPS mutant R6 had relatively high resistance to glyphosate at 1× and 2× dosages, and under the 5× glyphosate dosage, the proportion of the rice seedlings containing the rice EPSPS mutant R2 having medium and high glyphosate resistance was merely 3.4%, while the proportions of the rice seedlings containing the rice EPSPS mutants R3, R5 and R6 having medium and high glyphosate resistance were 13.4%, 42.1% and 63.3%, respectively, which are obviously higher than the resistance level of the rice seedlings containing R2, and under the 20× dosage, still 63.38% of the rice seedlings containing R6 had medium and high glyphosate resistance, indicating that the site mutation L214(195)P and the site mutation S267(247)G both could substantially further improve the glyphosate resistance on the basis of the glyphosate resistance provided by the site mutation P116(101)S, moreover, the combined glyphosate resistant of the mutant containing L214(195)P and the mutant containing S267(247)G was superior to that of the single mutant, which gives superposed effect.

The above results sufficiently indicate that compared with the *E. coli* EPSPS sequence, the amino acid sequence of the plant EPSPS mutant containing the mutation L195P corresponding to the site 195 of the *E. coli* EPSPS and/or containing the mutation S247G corresponding to the site 247 of the *E. coli* EPSPS can endow the plant EPSPS mutant with the glyphosate resistance in the plant or improve the glyphosate resistance of the plant EPSPS mutant in the plant.

The above-mentioned are merely for preferred examples of the present disclosure and not used to limit the present disclosure. For one skilled in the art, various modifications and changes may be made to the present disclosure. Any modifications, equivalent substitutions, improvements and so on made within the spirit and principle of the present disclosure, should be covered within the scope of protection of the present disclosure.

What is claimed is:

1. A plant 5-enolpyruvylshikimate-3-phosphate synthase (EPSPS) mutant protein, comprising a leucine to proline substitution at a position corresponding to position 195 of SEQ ID NO: 41 and/or comprising a serine to glycine substitution at a position corresponding to position 247 of SEQ ID NO: 41.

2. The plant EPSPS mutant protein of claim 1, further comprising a proline to serine substitution at a position corresponding to position 101 of SEQ ID NO: 41.

3. The plant EPSPS mutant protein of claim 1, wherein the protein is derived from a plant selected from the group consisting of: rice, tobacco, soybean, maize, wheat, cotton, rape, and sorghum.

4. The plant EPSPS mutant protein of claim 1, wherein the protein comprises an amino acid sequence selected from the group consisting of: SEQ ID NO: 4, SEQ ID NO: 8, SEQ ID NO: 10, SEQ ID NO: 12, SEQ ID NO: 16, SEQ ID NO: 20, SEQ ID NO: 22, SEQ ID NO: 24, SEQ ID NO: 26, SEQ ID NO: 30, SEQ ID NO: 34, SEQ ID NO: 36, SEQ ID NO: 38 and SEQ ID NO: 40.

5. A nucleic acid molecule encoding the mutant EPSPS protein of claim 1.

6. A method for preparing a glyphosate resistant plant, comprising transforming a target plant with the nucleic acid molecule of claim 5 or with a vector containing said molecule to obtain the glyphosate resistant plant.

7. The method of claim 6, wherein the target plant is selected from the group consisting of: wheat, rice, barley, oat, maize, sorghum, millet, buckwheat, maiden cane, mung bean, broad bean, pea, lentil, sweet potato, potato, cotton, soybean, rape plant, sesame, peanut, sunflower, radish, carrot, turnip, beet, Chinese cabbage, mustard, cabbage, cauliflower, Chinese kale, cucumber, zucchini, pumpkin, wax gourd, balsam pear, loofah, snake melon, watermelon, melon, tomato, eggplant, pepper, kidney bean, cowpea, green soy bean, Chinese chives, welsh onion, onion, leek, spinach, celery, amaranth, lettuce, crown daisy chrysanthemum, daylily, grape, strawberry, beet, sugarcane, tobacco, alfalfa, pasture grass, turfgrass, tea and cassava.

8. The plant EPSPS mutant protein of claim 2, wherein the protein is derived from a plant selected from the group consisting of: rice, tobacco, soybean, maize, wheat, cotton, rape, and sorghum.

* * * * *

SEQUENCE LISTING

```
<160> NUMBER OF SEQ ID NOS: 45

<210> SEQ ID NO 1
<211> LENGTH: 1359
<212> TYPE: DNA
<213> ORGANISM: Glycine max

<400> SEQUENCE: 1

atggccgccg cagagaagcc ttcgacggcg ccggagatcg tgttggaacc tatcaaagac     60

atctcgggta ccatcacatt gccagggtct aagtctctgt ccaatcgaat tttgcttctt    120

gctgctctct ctgagggaac aactgttgta gacaacttgc tgtacagcga ggatattcat    180

tacatgcttg gtgcattaag gacccttgga ctgcgtgtgg aagacgacca aacaaccaaa    240

caagcaattg tggaaggctg tgggggattg tttcccacta ttaaagaatc taaagatgaa    300

atcaatttat tccttggaaa tgctggtact gcgatgcgtc ctttgacagc agctgtagtt    360

gctgcaggtg gaaatgcaag ctacgtactt gatggagtgc cccgaatgag agagaggcca    420

attggggatt tggttgctgg tcttaagcag ctcggtgcag atgttgattg ctttcttggc    480

acaaactgtc cacctgttcg tgtaaatggg aagggaggac ttcctggcgg aaaggtgaaa    540

ctgtctggat cagttagcag tcaataccta actgctttgc ttatggcagc tcctttagct    600

cttggcgatg tggaaattga gattgttgat aaactgattt ctgttccata tgttgaaatg    660

actctgaagt tgatggagcg ttttggagtt tctgtggaac acagtggtga ttgggataag    720

ttcttggtcc atggaggtca aaagtacaag tctcctggca atgcttttgt tgaaggtgat    780

gcttcaagtg ccagttactt cctagctggt gcagcagtta ctggtgggac tatcactgtt    840

aatggctgtg gcacaagcag tttacaggga gatgtaaaat ttgctgaagt tcttgaaaag    900

atgggagcta aggttacatg gtcagagaac agtgtcaccg ttactggacc gccacaagat    960

tcttctggtc aaaaagtctt gcaaggcatt gatgtcaata tgaacaagat gccagatgtt   1020

gccatgactc ttgccgttgt cgcactattt gctaatggtc aaactaccat cagagatgtg   1080

gcaagttgga gagttaaaga gactgagagg atgatagcaa tctgcacaga actcagaaag   1140
```

-continued

```
ctaggagcaa cagttgaaga aggtcctgat tactgtgtga ttactccacc tgagaaattg   1200

aatgtcacag ctatagacac atatgatgac cacagaatgg ccatggcatt ctctcttgct   1260

gcttgtgggg atgttccagt aaccatcaag gatcctggtt gcaccaggaa gacatttccc   1320

gactactttg aagtccttga gaggttcaca aggcactaa                          1359


<210> SEQ ID NO 2
<211> LENGTH: 452
<212> TYPE: PRT
<213> ORGANISM: Glycine max

<400> SEQUENCE: 2

Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
            20                  25                  30

Leu Ser Asn Arg Ile Leu Leu Leu Ala Ala Leu Ser Glu Gly Thr Thr
        35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Pro Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Ser Tyr Phe Leu Ala Gly Ala Ala
            260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
    290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335
```

-continued

Met Pro Asp Val Ala Met Thr Leu Ala Val Val Ala Leu Phe Ala Asn
340 345 350

Gly Gln Thr Thr Ile Arg Asp Val Ala Ser Trp Arg Val Lys Glu Thr
355 360 365

Glu Arg Met Ile Ala Ile Cys Thr Glu Leu Arg Lys Leu Gly Ala Thr
370 375 380

Val Glu Glu Gly Pro Asp Tyr Cys Val Ile Thr Pro Pro Glu Lys Leu
385 390 395 400

Asn Val Thr Ala Ile Asp Thr Tyr Asp Asp His Arg Met Ala Met Ala
405 410 415

Phe Ser Leu Ala Ala Cys Gly Asp Val Pro Val Thr Ile Lys Asp Pro
420 425 430

Gly Cys Thr Arg Lys Thr Phe Pro Asp Tyr Phe Glu Val Leu Glu Arg
435 440 445

Phe Thr Arg His
450

<210> SEQ ID NO 3
<211> LENGTH: 1359
<212> TYPE: DNA
<213> ORGANISM: Artificial Sequence
<220> FEATURE:
<223> OTHER INFORMATION: Description of Artificial Sequence: Synthetic polynucleotide encoding Glycine max EPSPS mutant with mutation L212(195)P

<400> SEQUENCE: 3
atggccgccg cagagaagcc ttcgacggcg ccggagatcg tgttggaacc tatcaaagac 60
atctcgggta ccatcacatt gccagggtct aagtctctgt ccaatcgaat tttgcttctt 120
gctgctctct ctgagggaac aactgttgta gacaacttgc tgtacagcga ggatattcat 180
tacatgcttg gtgcattaag gacccttgga ctgcgtgtgg aagacgacca aacaaccaaa 240
caagcaattg tggaaggctg tgggggattg tttcccacta ttaaagaatc taaagatgaa 300
atcaatttat tccttggaaa tgctggtact gcgatgcgtc ctttgacagc agctgtagtt 360
gctgcaggtg gaaatgcaag ctacgtactt gatggagtgc cccgaatgag agagaggcca 420
attggggatt tggttgctgg tcttaagcag ctcggtgcag atgttgattg ctttcttggc 480
acaaactgtc cacctgttcg tgtaaatggg aagggaggac ttcctggcgg aaaggtgaaa 540
ctgtctggat cagttagcag tcaataccta actgctttgc ttatggcagc tcctttagct 600
cttggcgatg tggaaattga gattgttgat aaaccgattt ctgttccata tgttgaaatg 660
actctgaagt tgatggagcg ttttggagtt tctgtggaac acagtggtga ttgggataag 720
ttcttggtcc atggaggtca aaagtacaag tctcctggca atgcttttgt tgaaggtgat 780
gcttcaagtg ccagttactt cctagctggt gcagcagtta ctggtgggac tatcactgtt 840
aatggctgtg gcacaagcag tttacaggga gatgtaaaat ttgctgaagt tcttgaaaag 900
atgggagcta aggttacatg gtcagagaac agtgtcaccg ttactggacc gccacaagat 960
tcttctggtc aaaaagtctt gcaaggcatt gatgtcaata tgaacaagat gccagatgtt 1020
gccatgactc ttgccgttgt cgcactattt gctaatggtc aaactaccat cagagatgtg 1080
gcaagttgga gagttaaaga gactgagagg atgatagcaa tctgcacaga actcagaaag 1140
ctaggagcaa cagttgaaga aggtcctgat tactgtgtga ttactccacc tgagaaattg 1200
aatgtcacag ctatagacac atatgatgac cacagaatgg ccatggcatt ctctcttgct 1260
gcttgtgggg atgttccagt aaccatcaag gatcctggtt gcaccaggaa gacatttccc 1320
gactactttg aagtccttga gaggttcaca aggcactaa 1359

<210> SEQ ID NO 4
<211> LENGTH: 452
<212> TYPE: PRT
<213> ORGANISM: Artificial Sequence
<220> FEATURE:
<223> OTHER INFORMATION: Description of Artificial Sequence: Synthetic
Glycine max EPSPS mutant with mutation L212(195)P
polypeptide

<400> SEQUENCE: 4

```
Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
            20                  25                  30

Leu Ser Asn Arg Ile Leu Leu Leu Ala Ala Leu Ser Glu Gly Thr Thr
        35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Pro Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Pro Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Ser Tyr Phe Leu Ala Gly Ala Ala
            260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
    290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335
```

```
Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
        435                 440                 445

Phe Thr Arg His
    450


<210> SEQ ID NO 5
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide encoding Glycine max EPSPS mutant with mutation
      P114(101)S

<400> SEQUENCE: 5

atggccgccg cagagaagcc ttcgacggcg ccggagatcg tgttggaacc tatcaaagac      60

atctcgggta ccatcacatt gccagggtct aagtctctgt ccaatcgaat tttgcttctt     120

gctgctctct ctgagggaac aactgttgta gacaacttgc tgtacagcga ggatattcat     180

tacatgcttg gtgcattaag gacccttgga ctgcgtgtgg aagacgacca aacaaccaaa     240

caagcaattg tggaaggctg tgggggattg tttcccacta ttaaagaatc taaagatgaa     300

atcaatttat tccttggaaa tgctggtact gcgatgcgta gcttgacagc agctgtagtt     360

gctgcaggtg gaaatgcaag ctacgtactt gatggagtgc cccgaatgag agagaggcca     420

attggggatt tggttgctgg tcttaagcag ctcggtgcag atgttgattg ctttcttggc     480

acaaactgtc cacctgttcg tgtaaatggg aagggaggac ttcctggcgg aaaggtgaaa     540

ctgtctggat cagttagcag tcaataccta actgctttgc ttatggcagc tcctttagct     600

cttggcgatg tggaaattga gattgttgat aaactgattt ctgttccata tgttgaaatg     660

actctgaagt tgatggagcg ttttggagtt tctgtggaac acagtggtga ttgggataag     720

ttcttggtcc atggaggtca aaagtacaag tctcctggca atgcttttgt tgaaggtgat     780

gcttcaagtg ccagttactt cctagctggt gcagcagtta ctggtgggac tatcactgtt     840

aatggctgtg gcacaagcag tttacaggga gatgtaaaat ttgctgaagt tcttgaaaag     900

atgggagcta aggttacatg gtcagagaac agtgtcaccg ttactggacc gccacaagat     960

tcttctggtc aaaaagtctt gcaaggcatt gatgtcaata tgaacaagat gccagatgtt    1020

gccatgactc ttgccgttgt cgcactattt gctaatggtc aaactaccat cagagatgtg    1080

gcaagttgga gagttaaaga gactgagagg atgatagcaa tctgcacaga actcagaaag    1140

ctaggagcaa cagttgaaga aggtcctgat tactgtgtga ttactccacc tgagaaattg    1200

aatgtcacag ctatagacac atatgatgac cacagaatgg ccatggcatt ctctcttgct    1260
```

-continued

```
gcttgtgggg atgttccagt aaccatcaag gatcctggtt gcaccaggaa gacatttccc   1320

gactactttg aagtccttga gaggttcaca aggcactaa                          1359


<210> SEQ ID NO 6
<211> LENGTH: 452
<212> TYPE: PRT
<213> ORGANISM: Artificial Sequence
<220> FEATURE:
<223> OTHER INFORMATION: Description of Artificial Sequence: Synthetic
      Glycine max EPSPS mutant with mutation P114(101)S
      polypeptide

<400> SEQUENCE: 6

Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
            20                  25                  30

Leu Ser Asn Arg Ile Leu Leu Leu Ala Ala Leu Ser Glu Gly Thr Thr
        35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Ser Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Ser Tyr Phe Leu Ala Gly Ala Ala
            260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
    290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335
```

-continued

```
Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
        435                 440                 445

Phe Thr Arg His
    450


<210> SEQ ID NO 7
<211> LENGTH: 1359
<212> TYPE: DNA
<213> ORGANISM: Artificial sequence
<220> FEATURE:
<223> OTHER INFORMATION: Description of Artificial Sequence: Synthetic
      polynucleotide encoding Glycine max EPSPS mutant with mutations
      L212(195)P and P114(101)S

<400> SEQUENCE: 7

atggccgccg cagagaagcc ttcgacggcg ccggagatcg tgttggaacc tatcaaagac     60

atctcgggta ccatcacatt gccagggtct aagtctctgt ccaatcgaat tttgcttctt    120

gctgctctct ctgagggaac aactgttgta gacaacttgc tgtacagcga ggatattcat    180

tacatgcttg gtgcattaag gacccttgga ctgcgtgtgg aagacgacca aacaaccaaa    240

caagcaattg tggaaggctg tgggggattg tttcccacta ttaaagaatc taaagatgaa    300

atcaatttat tccttggaaa tgctggtact gcgatgcgta gcttgacagc agctgtagtt    360

gctgcaggtg gaaatgcaag ctacgtactt gatggagtgc cccgaatgag agagaggcca    420

attggggatt tggttgctgg tcttaagcag ctcggtgcag atgttgattg ctttcttggc    480

acaaactgtc cacctgttcg tgtaaatggg aagggaggac ttcctggcgg aaaggtgaaa    540

ctgtctggat cagttagcag tcaataccta actgctttgc ttatggcagc tcctttagct    600

cttggcgatg tggaaattga gattgttgat aaaccgattt ctgttccata tgttgaaatg    660

actctgaagt tgatggagcg ttttggagtt tctgtggaac acagtggtga ttgggataag    720

ttcttggtcc atggaggtca aaagtacaag tctcctggca atgcttttgt tgaaggtgat    780

gcttcaagtg ccagttactt cctagctggt gcagcagtta ctggtgggac tatcactgtt    840

aatggctgtg gcacaagcag tttacaggga gatgtaaaat ttgctgaagt tcttgaaaag    900

atgggagcta aggttacatg gtcagagaac agtgtcaccg ttactggacc gccacaagat    960

tcttctggtc aaaaagtctt gcaaggcatt gatgtcaata tgaacaagat gccagatgtt   1020

gccatgactc ttgccgttgt cgcactattt gctaatggtc aaactaccat cagagatgtg   1080

gcaagttgga gagttaaaga gactgagagg atgatagcaa tctgcacaga actcagaaag   1140

ctaggagcaa cagttgaaga aggtcctgat tactgtgtga ttactccacc tgagaaattg   1200

aatgtcacag ctatagacac atatgatgac cacagaatgg ccatggcatt ctctcttgct   1260
```

```
gcttgtgggg atgttccagt aaccatcaag gatcctggtt gcaccaggaa gacatttccc   1320

gactactttg aagtccttga gaggttcaca aggcactaa                          1359


<210> SEQ ID NO 8
<211> LENGTH: 452
<212> TYPE: PRT
<213> ORGANISM: Artificial Sequence
<220> FEATURE:
<223> OTHER INFORMATION: Description of Artificial Sequence: Synthetic
      Glycine max EPSPS mutant with mutations L212(195)P and
      P114(101)S polypeptide

<400> SEQUENCE: 8

Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
            20                  25                  30

Leu Ser Asn Arg Ile Leu Leu Leu Ala Ala Leu Ser Glu Gly Thr Thr
        35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Ser Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Pro Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Ser Tyr Phe Leu Ala Gly Ala Ala
            260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
    290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335
```

-continued

```
Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
        435                 440                 445

Phe Thr Arg His
    450


<210> SEQ ID NO 9
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide encoding Glycine max EPSPS mutant with mutation
      S265(247)G

<400> SEQUENCE: 9

atggccgccg cagagaagcc ttcgacggcg ccggagatcg tgttggaacc tatcaaagac     60

atctcgggta ccatcacatt gccagggtct aagtctctgt ccaatcgaat tttgcttctt    120

gctgctctct ctgagggaac aactgttgta gacaacttgc tgtacagcga ggatattcat    180

tacatgcttg gtgcattaag gacccttgga ctgcgtgtgg aagacgacca aacaaccaaa    240

caagcaattg tggaaggctg tgggggattg tttcccacta ttaaagaatc taaagatgaa    300

atcaatttat tccttggaaa tgctggtact gcgatgcgtc ctttgacagc agctgtagtt    360

gctgcaggtg gaaatgcaag ctacgtactt gatggagtgc cccgaatgag agagaggcca    420

attggggatt tggttgctgg tcttaagcag ctcggtgcag atgttgattg ctttcttggc    480

acaaactgtc cacctgttcg tgtaaatggg aagggaggac ttcctggcgg aaaggtgaaa    540

ctgtctggat cagttagcag tcaataccta actgctttgc ttatggcagc tcctttagct    600

cttggcgatg tggaaattga gattgttgat aaactgattt ctgttccata tgttgaaatg    660

actctgaagt tgatggagcg ttttggagtt tctgtggaac acagtggtga ttgggataag    720

ttcttggtcc atggaggtca aaagtacaag tctcctggca atgcttttgt tgaaggtgat    780

gcttcaagtg ccggctactt cctagctggt gcagcagtta ctggtgggac tatcactgtt    840

aatggctgtg gcacaagcag tttacaggga gatgtaaaat ttgctgaagt tcttgaaaag    900

atgggagcta aggttacatg gtcagagaac agtgtcaccg ttactggacc gccacaagat    960

tcttctggtc aaaaagtctt gcaaggcatt gatgtcaata tgaacaagat gccagatgtt   1020

gccatgactc ttgccgttgt cgcactattt gctaatggtc aaactaccat cagagatgtg   1080

gcaagttgga gagttaaaga gactgagagg atgatagcaa tctgcacaga actcagaaag   1140

ctaggagcaa cagttgaaga aggtcctgat tactgtgtga ttactccacc tgagaaattg   1200

aatgtcacag ctatagacac atatgatgac cacagaatgg ccatggcatt ctctcttgct   1260
```

-continued

```
gcttgtgggg atgttccagt aaccatcaag gatcctggtt gcaccaggaa gacatttccc   1320

gactactttg aagtccttga gaggttcaca aggcactaa                          1359


<210> SEQ ID NO 10
<211> LENGTH: 452
<212> TYPE: PRT
<213> ORGANISM: Artificial Sequence
<220> FEATURE:
<223> OTHER INFORMATION: Description of Artificial Sequence: Synthetic
      Glycine max EPSPS mutant with mutation S265(247)G
      polypeptide

<400> SEQUENCE: 10

Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
            20                  25                  30

Leu Ser Asn Arg Ile Leu Leu Leu Ala Ala Leu Ser Glu Gly Thr Thr
        35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Pro Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Gly Tyr Phe Leu Ala Gly Ala Ala
            260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
    290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335
```

-continued

```
Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
        435                 440                 445

Phe Thr Arg His
    450
```

<210> SEQ ID NO 11
<211> LENGTH: 1359
<212> TYPE: DNA
<213> ORGANISM: Artificial Sequence
<220> FEATURE:
<223> OTHER INFORMATION: Description of Artificial Sequence: Synthetic polynucleotide encoding Glycine max EPSPS mutant with mutations S265(247)G and P114(101)S

<400> SEQUENCE: 11

```
atggccgccg cagagaagcc ttcgacggcg ccggagatcg tgttggaacc tatcaaagac      60

atctcgggta ccatcacatt gccagggtct aagtctctgt ccaatcgaat tttgcttctt     120

gctgctctct ctgagggaac aactgttgta gacaacttgc tgtacagcga ggatattcat     180

tacatgcttg gtgcattaag gacccttgga ctgcgtgtgg aagacgacca aacaaccaaa     240

caagcaattg tggaaggctg tgggggattg tttcccacta ttaaagaatc taaagatgaa     300

atcaatttat tccttggaaa tgctggtact gcgatgcgta gcttgacagc agctgtagtt     360

gctgcaggtg gaaatgcaag ctacgtactt gatggagtgc cccgaatgag agagaggcca     420

attggggatt tggttgctgg tcttaagcag ctcggtgcag atgttgattg ctttcttggc     480

acaaactgtc cacctgttcg tgtaaatggg aagggaggac ttcctggcgg aaaggtgaaa     540

ctgtctggat cagttagcag tcaataccta actgctttgc ttatggcagc tcctttagct     600

cttggcgatg tggaaattga gattgttgat aaactgattt ctgttccata tgttgaaatg     660

actctgaagt tgatggagcg ttttggagtt tctgtggaac acagtggtga ttgggataag     720

ttcttggtcc atggaggtca aaagtacaag tctcctggca atgcttttgt tgaaggtgat     780

gcttcaagtg ccggctactt cctagctggt gcagcagtta ctggtgggac tatcactgtt     840

aatggctgtg gcacaagcag tttacaggga gatgtaaaat ttgctgaagt tcttgaaaag     900

atgggagcta aggttacatg gtcagagaac agtgtcaccg ttactggacc gccacaagat     960

tcttctggtc aaaaagtctt gcaaggcatt gatgtcaata tgaacaagat gccagatgtt    1020

gccatgactc ttgccgttgt cgcactattt gctaatggtc aaactaccat cagagatgtg    1080

gcaagttgga gagttaaaga gactgagagg atgatagcaa tctgcacaga actcagaaag    1140

ctaggagcaa cagttgaaga aggtcctgat tactgtgtga ttactccacc tgagaaattg    1200

aatgtcacag ctatagacac atatgatgac cacagaatgg ccatggcatt ctctcttgct    1260
```

gcttgtgggg atgttccagt aaccatcaag gatcctggtt gcaccaggaa gacatttccc 1320
gactactttg aagtccttga gaggttcaca aggcactaa 1359

<210> SEQ ID NO 12
<211> LENGTH: 452
<212> TYPE: PRT
<213> ORGANISM: Artificial Sequence
<220> FEATURE:
<223> OTHER INFORMATION: Description of Artificial Sequence: Synthetic
Glycine max EPSPS mutant with mutations S265(247)G and
P114(101)S polypeptide

<400> SEQUENCE: 12

```
Met Ala Ala Ala Glu Lys Pro Ser Thr Ala Pro Glu Ile Val Leu Glu
1               5                   10                  15

Pro Ile Lys Asp Ile Ser Gly Thr Ile Thr Leu Pro Gly Ser Lys Ser
            20                  25                  30

Leu Ser Asn Arg Ile Leu Leu Leu Ala Ala Leu Ser Glu Gly Thr Thr
        35                  40                  45

Val Val Asp Asn Leu Leu Tyr Ser Glu Asp Ile His Tyr Met Leu Gly
    50                  55                  60

Ala Leu Arg Thr Leu Gly Leu Arg Val Glu Asp Asp Gln Thr Thr Lys
65                  70                  75                  80

Gln Ala Ile Val Glu Gly Cys Gly Gly Leu Phe Pro Thr Ile Lys Glu
                85                  90                  95

Ser Lys Asp Glu Ile Asn Leu Phe Leu Gly Asn Ala Gly Thr Ala Met
            100                 105                 110

Arg Ser Leu Thr Ala Ala Val Val Ala Ala Gly Gly Asn Ala Ser Tyr
        115                 120                 125

Val Leu Asp Gly Val Pro Arg Met Arg Glu Arg Pro Ile Gly Asp Leu
    130                 135                 140

Val Ala Gly Leu Lys Gln Leu Gly Ala Asp Val Asp Cys Phe Leu Gly
145                 150                 155                 160

Thr Asn Cys Pro Pro Val Arg Val Asn Gly Lys Gly Gly Leu Pro Gly
                165                 170                 175

Gly Lys Val Lys Leu Ser Gly Ser Val Ser Ser Gln Tyr Leu Thr Ala
            180                 185                 190

Leu Leu Met Ala Ala Pro Leu Ala Leu Gly Asp Val Glu Ile Glu Ile
        195                 200                 205

Val Asp Lys Leu Ile Ser Val Pro Tyr Val Glu Met Thr Leu Lys Leu
    210                 215                 220

Met Glu Arg Phe Gly Val Ser Val Glu His Ser Gly Asp Trp Asp Lys
225                 230                 235                 240

Phe Leu Val His Gly Gly Gln Lys Tyr Lys Ser Pro Gly Asn Ala Phe
                245                 250                 255

Val Glu Gly Asp Ala Ser Ser Ala Gly Tyr Phe Leu Ala Gly Ala Ala
            260                 265                 270

Val Thr Gly Gly Thr Ile Thr Val Asn Gly Cys Gly Thr Ser Ser Leu
        275                 280                 285

Gln Gly Asp Val Lys Phe Ala Glu Val Leu Glu Lys Met Gly Ala Lys
    290                 295                 300

Val Thr Trp Ser Glu Asn Ser Val Thr Val Thr Gly Pro Pro Gln Asp
305                 310                 315                 320

Ser Ser Gly Gln Lys Val Leu Gln Gly Ile Asp Val Asn Met Asn Lys
                325                 330                 335
```

-continued

```
Met Pro Asp Val Ala Met Thr Leu Ala Val Val Ala Leu Phe Ala Asn
            340                 345                 350

Gly Gln Thr Thr Ile Arg Asp Val Ala Ser Trp Arg Val Lys Glu Thr
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Val Leu Glu Arg
        435                 440                 445

Phe Thr Arg His
    450


<210> SEQ ID NO 13
<211> LENGTH: 1371
<212> TYPE: DNA
<213> ORGANISM: Triticum aestivum

<400> SEQUENCE: 13

atggcgacgt ccgtggcggc ccccgcggcg cccgcgggcg ccgaggaggt cgtgctgcag      60

cccatccgcg agatctccgg cgccgtgcag ctgcccggct ccaagtcgct ctccaaccgg     120

atcctcctcc tctccgccct ctccgaggga acaacggtgg tggataacct gttgaacagt     180

gaggatgtcc actacatgct tgaggccctg gaagcccttg gactctccgt ggaagcagat     240

aaagttgcaa aaagagctgt ggttgttggc tgtggcggca ggttcccagt cgaaaaggac     300

gccaaagagg aagtaaagct cttcttgggt aatgctggaa ctgcaatgcg gccactgacg     360

gcagctgtag tagctgctgg tggaaatgca acttatgtgc ttgatggcgt accaagaatg     420

agggagcgac ctattggtga cttagttgta ggtttgcaac aactcggcgc agatgtcgat     480

tgtttccttg gcacaaactg cccacctgtc cgtatcaacg gcaaaggagg tctacctggt     540

ggcaaggtta agctctctgg ttccattagc agtcaatacc tgagttcctt gctgatggct     600

gctcctttgg ctcttgagga tgtcgagatt gaaatcattg ataaactgat ctccgttcct     660

tatgttgaaa tgacattgaa attgatggag cattttggtg tgactgcgga gcattctgat     720

agttgggaca gattctacat taagggagga caaaaataca agtcccctgg aaatgcctat     780

gtcgaaggtg atgcctcaag tgcgagctat ttcttggctg gtgctgccat caccggaggg     840

actgtgactg tcgaaggttg cggcaccact agtttgcagg gtgatgtgaa atttgctgag     900

gtacttgaaa tgatgggagc aaaggtcaca tggactgaca ctagtgtaac tgttactggc     960

ccaccgcgtc agccatttgg aaggaaacac ctaaaagctg ttgatgtcaa catgaacaaa    1020

atgccagatg tcgcgatgac tctagccgtt gttgccctgt ttgccgatgg tccaaccgct    1080

atcagagatg ttgcctcctg gagagtgaag gaaactgaaa gaatggtcgc gatccggacc    1140

gagctgacga agctgggagc aacggtggag gaaggcccgg actactgcat catcacgccg    1200

ccggagaagc tgaacatcac ggcgatcgac acctacgatg accaccggat ggcgatggcc    1260

ttctccctgg cggcctgtgc tgaggtgcca gtcaccatca gggaccctgg atgcacccga    1320

aagaccttcc ccaactactt cgacgtgcta agcaccttcg tcaagaacta g             1371
```

<210> SEQ ID NO 14
<211> LENGTH: 456
<212> TYPE: PRT
<213> ORGANISM: Triticum aestivum

<400> SEQUENCE: 14

```
Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
            100                 105                 110

Gly Thr Ala Met Arg Pro Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Leu Ile Ser Val Pro Tyr Val Glu Met
    210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Ser Tyr Phe Leu
            260                 265                 270

Ala Gly Ala Ala Ile Thr Gly Gly Thr Val Thr Val Glu Gly Cys Gly
        275                 280                 285

Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380
```

Leu Gly Ala Thr Val Glu Glu Gly Pro Asp Tyr Cys Ile Ile Thr Pro
385 390 395 400

Pro Glu Lys Leu Asn Ile Thr Ala Ile Asp Thr Tyr Asp Asp His Arg
405 410 415

Met Ala Met Ala Phe Ser Leu Ala Ala Cys Ala Glu Val Pro Val Thr
420 425 430

Ile Arg Asp Pro Gly Cys Thr Arg Lys Thr Phe Pro Asn Tyr Phe Asp
435 440 445

Val Leu Ser Thr Phe Val Lys Asn
450 455

<210> SEQ ID NO 15
<211> LENGTH: 1371
<212> TYPE: DNA
<213> ORGANISM: Artificial sequence
<220> FEATURE:
<223> OTHER INFORMATION: Description of Artificial Sequence: Synthetic polynucleotide encoding Triticum aestivum EPSPS mutant with mutation S269(247)G

<400> SEQUENCE: 15
atggcgacgt ccgtggcggc ccccgcggcg cccgcgggcg ccgaggaggt cgtgctgcag 60
cccatccgcg agatctccgg cgccgtgcag ctgcccggct ccaagtcgct ctccaaccgg 120
atcctcctcc tctccgccct ctccgaggga acaacggtgg tggataacct gttgaacagt 180
gaggatgtcc actacatgct tgaggccctg gaagcccttg gactctccgt ggaagcagat 240
aaagttgcaa aaagagctgt ggttgttggc tgtggcggca ggttcccagt cgaaaaggac 300
gccaaagagg aagtaaagct cttcttgggt aatgctggaa ctgcaatgcg gccactgacg 360
gcagctgtag tagctgctgg tggaaatgca acttatgtgc ttgatggcgt accaagaatg 420
agggagcgac ctattggtga cttagttgta ggtttgcaac aactcggcgc agatgtcgat 480
tgtttccttg gcacaaactg cccacctgtc cgtatcaacg gcaaaggagg tctacctggt 540
ggcaaggtta agctctctgg ttccattagc agtcaatacc tgagttcctt gctgatggct 600
gctcctttgg ctcttgagga tgtcgagatt gaaatcattg ataaactgat ctccgttcct 660
tatgttgaaa tgacattgaa attgatggag cattttggtg tgactgcgga gcattctgat 720
agttgggaca gattctacat taagggagga caaaaataca agtcccctgg aaatgcctat 780
gtcgaaggtg atgcctcaag tgcgggctat ttcttggctg gtgctgccat caccggaggg 840
actgtgactg tcgaaggttg cggcaccact agtttgcagg gtgatgtgaa atttgctgag 900
gtacttgaaa tgatgggagc aaaggtcaca tggactgaca ctagtgtaac tgttactggc 960
ccaccgcgtc agccatttgg aaggaaacac ctaaaagctg ttgatgtcaa catgaacaaa 1020
atgccagatg tcgcgatgac tctagccgtt gttgccctgt ttgccgatgg tccaaccgct 1080
atcagagatg ttgcctcctg gagagtgaag gaaactgaaa gaatggtcgc gatccggacc 1140
gagctgacga agctgggagc aacggtggag gaaggcccgg actactgcat catcacgccg 1200
ccggagaagc tgaacatcac ggcgatcgac acctacgatg accaccggat ggcgatggcc 1260
ttctccctgg cggcctgtgc tgaggtgcca gtcaccatca gggaccctgg atgcacccga 1320
aagaccttcc ccaactactt cgacgtgcta agcaccttcg tcaagaacta g 1371

<210> SEQ ID NO 16
<211> LENGTH: 456
<212> TYPE: PRT
<213> ORGANISM: Artificial Sequence
<220> FEATURE:
<223> OTHER INFORMATION: Description of Artificial Sequence: Synthetic
Triticum aestivum EPSPS mutant with mutation S269(247)G
polypeptide

<400> SEQUENCE: 16

```
Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
            100                 105                 110

Gly Thr Ala Met Arg Pro Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Leu Ile Ser Val Pro Tyr Val Glu Met
    210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Gly Tyr Phe Leu
            260                 265                 270

Ala Gly Ala Ala Ile Thr Gly Gly Thr Val Thr Val Glu Gly Cys Gly
        275                 280                 285

Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380
```

-continued

```
Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
        435                 440                 445

Val Leu Ser Thr Phe Val Lys Asn
    450                 455


<210> SEQ ID NO 17
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide encoding Triticum aestivum EPSPS mutant with
      mutation P118(101)S

<400> SEQUENCE: 17

atggcgacgt ccgtggcggc ccccgcggcg cccgcgggcg ccgaggaggt cgtgctgcag      60

cccatccgcg agatctccgg cgccgtgcag ctgcccggct ccaagtcgct ctccaaccgg     120

atcctcctcc tctccgccct ctccgaggga acaacggtgg tggataacct gttgaacagt     180

gaggatgtcc actacatgct tgaggccctg gaagcccttg gactctccgt ggaagcagat     240

aaagttgcaa aaagagctgt ggttgttggc tgtggcggca ggttcccagt cgaaaaggac     300

gccaaagagg aagtaaagct cttcttgggt aatgctggaa ctgcaatgcg gagcctgacg     360

gcagctgtag tagctgctgg tggaaatgca acttatgtgc ttgatggcgt accaagaatg     420

agggagcgac ctattggtga cttagttgta ggtttgcaac aactcggcgc agatgtcgat     480

tgtttccttg gcacaaactg cccacctgtc cgtatcaacg gcaaaggagg tctacctggt     540

ggcaaggtta agctctctgg ttccattagc agtcaatacc tgagttcctt gctgatggct     600

gctcctttgg ctcttgagga tgtcgagatt gaaatcattg ataaactgat ctccgttcct     660

tatgttgaaa tgacattgaa attgatggag cattttggtg tgactgcgga gcattctgat     720

agttgggaca gattctacat taagggagga caaaaataca agtcccctgg aaatgcctat     780

gtcgaaggtg atgcctcaag tgcgagctat ttcttggctg gtgctgccat caccggaggg     840

actgtgactg tcgaaggttg cggcaccact agtttgcagg gtgatgtgaa atttgctgag     900

gtacttgaaa tgatgggagc aaaggtcaca tggactgaca ctagtgtaac tgttactggc     960

ccaccgcgtc agccatttgg aaggaaacac ctaaaagctg ttgatgtcaa catgaacaaa    1020

atgccagatg tcgcgatgac tctagccgtt gttgccctgt ttgccgatgg tccaaccgct    1080

atcagagatg ttgcctcctg gagagtgaag gaaactgaaa gaatggtcgc gatccggacc    1140

gagctgacga agctgggagc aacggtggag gaaggcccgg actactgcat catcacgccg    1200

ccggagaagc tgaacatcac ggcgatcgac acctacgatg accaccggat ggcgatggcc    1260

ttctccctgg cggcctgtgc tgaggtgcca gtcaccatca gggaccctgg atgcacccga    1320

aagaccttcc ccaactactt cgacgtgcta agcaccttcg tcaagaacta g             1371


<210> SEQ ID NO 18
<211> LENGTH: 456
<212> TYPE: PRT
<213> ORGANISM: Artificial Sequence
<220> FEATURE:
```

-continued

```
<223> OTHER INFORMATION: Description of Artificial Sequence: Synthetic
      Triticum aestivum EPSPS mutant with mutation P118(101)S
      polypeptide

<400> SEQUENCE: 18

Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
            100                 105                 110

Gly Thr Ala Met Arg Ser Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Leu Ile Ser Val Pro Tyr Val Glu Met
    210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Ser Tyr Phe Leu
            260                 265                 270

Ala Gly Ala Ala Ile Thr Gly Gly Thr Val Thr Val Glu Gly Cys Gly
        275                 280                 285

Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380
```

-continued

Leu Gly Ala Thr Val Glu Glu Gly Pro Asp Tyr Cys Ile Ile Thr Pro
385 390 395 400

Pro Glu Lys Leu Asn Ile Thr Ala Ile Asp Thr Tyr Asp Asp His Arg
405 410 415

Met Ala Met Ala Phe Ser Leu Ala Ala Cys Ala Glu Val Pro Val Thr
420 425 430

Ile Arg Asp Pro Gly Cys Thr Arg Lys Thr Phe Pro Asn Tyr Phe Asp
435 440 445

Val Leu Ser Thr Phe Val Lys Asn
450 455

<210> SEQ ID NO 19
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide encoding Triticum aestivum EPSPS mutant with mutations S269(247)G and P118(101)S

<400> SEQUENCE: 19
atggcgacgt ccgtggcggc ccccgcggcg cccgcgggcg ccgaggaggt cgtgctgcag 60
cccatccgcg agatctccgg cgccgtgcag ctgcccggct ccaagtcgct ctccaaccgg 120
atcctcctcc tctccgccct ctccgaggga acaacggtgg tggataacct gttgaacagt 180
gaggatgtcc actacatgct tgaggccctg gaagcccttg gactctccgt ggaagcagat 240
aaagttgcaa aaagagctgt ggttgttggc tgtggcggca ggttcccagt cgaaaaggac 300
gccaaagagg aagtaaagct cttcttgggt aatgctggaa ctgcaatgcg gagcctgacg 360
gcagctgtag tagctgctgg tggaaatgca acttatgtgc ttgatggcgt accaagaatg 420
agggagcgac ctattggtga cttagttgta ggtttgcaac aactcggcgc agatgtcgat 480
tgtttccttg gcacaaactg cccacctgtc cgtatcaacg gcaaaggagg tctacctggt 540
ggcaaggtta agctctctgg ttccattagc agtcaatacc tgagttcctt gctgatggct 600
gctcctttgg ctcttgagga tgtcgagatt gaaatcattg ataaactgat ctccgttcct 660
tatgttgaaa tgacattgaa attgatggag cattttggtg tgactgcgga gcattctgat 720
agttgggaca gattctacat taagggagga caaaaataca agtcccctgg aaatgcctat 780
gtcgaaggtg atgcctcaag tgcgggctat ttcttggctg gtgctgccat caccggaggg 840
actgtgactg tcgaaggttg cggcaccact agtttgcagg gtgatgtgaa atttgctgag 900
gtacttgaaa tgatgggagc aaaggtcaca tggactgaca ctagtgtaac tgttactggc 960
ccaccgcgtc agccatttgg aaggaaacac ctaaaagctg ttgatgtcaa catgaacaaa 1020
atgccagatg tcgcgatgac tctagccgtt gttgccctgt ttgccgatgg tccaaccgct 1080
atcagagatg ttgcctcctg gagagtgaag gaaactgaaa gaatggtcgc gatccggacc 1140
gagctgacga agctgggagc aacggtggag gaaggcccgg actactgcat catcacgccg 1200
ccggagaagc tgaacatcac ggcgatcgac acctacgatg accaccggat ggcgatggcc 1260
ttctccctgg cggcctgtgc tgaggtgcca gtcaccatca gggaccctgg atgcacccga 1320
aagaccttcc ccaactactt cgacgtgcta agcaccttcg tcaagaacta g 1371

<210> SEQ ID NO 20
<211> LENGTH: 456
<212> TYPE: PRT
<213> ORGANISM: Artificial Sequence -continued
<220> FEATURE:
<223> OTHER INFORMATION: Description of Artificial Sequence: Synthetic Triticum aestivum EPSPS mutant with mutations S269(247)G and P118(101)S polypeptide

<400> SEQUENCE: 20

Met Ala Thr Ser Val Ala Ala Pro Ala Ala Pro Ala Gly Ala Glu Glu
1 5 10 15

Val Val Leu Gln Pro Ile Arg Glu Ile Ser Gly Ala Val Gln Leu Pro
20 25 30

Gly Ser Lys Ser Leu Ser Asn Arg Ile Leu Leu Leu Ser Ala Leu Ser
35 40 45

Glu Gly Thr Thr Val Val Asp Asn Leu Leu Asn Ser Glu Asp Val His
50 55 60

Tyr Met Leu Glu Ala Leu Glu Ala Leu Gly Leu Ser Val Glu Ala Asp
65 70 75 80

Lys Val Ala Lys Arg Ala Val Val Val Gly Cys Gly Gly Arg Phe Pro
85 90 95

Val Glu Lys Asp Ala Lys Glu Glu Val Lys Leu Phe Leu Gly Asn Ala
100 105 110

Gly Thr Ala Met Arg Ser Leu Thr Ala Ala Val Val Ala Ala Gly Gly
115 120 125

Asn Ala Thr Tyr Val Leu Asp Gly Val Pro Arg Met Arg Glu Arg Pro
130 135 140

Ile Gly Asp Leu Val Val Gly Leu Gln Gln Leu Gly Ala Asp Val Asp
145 150 155 160

Cys Phe Leu Gly Thr Asn Cys Pro Pro Val Arg Ile Asn Gly Lys Gly
165 170 175

Gly Leu Pro Gly Gly Lys Val Lys Leu Ser Gly Ser Ile Ser Ser Gln
180 185 190

Tyr Leu Ser Ser Leu Leu Met Ala Ala Pro Leu Ala Leu Glu Asp Val
195 200 205

Glu Ile Glu Ile Ile Asp Lys Leu Ile Ser Val Pro Tyr Val Glu Met
210 215 220

Thr Leu Lys Leu Met Glu His Phe Gly Val Thr Ala Glu His Ser Asp
225 230 235 240

Ser Trp Asp Arg Phe Tyr Ile Lys Gly Gly Gln Lys Tyr Lys Ser Pro
245 250 255

Gly Asn Ala Tyr Val Glu Gly Asp Ala Ser Ser Ala Gly Tyr Phe Leu
260 265 270

Ala Gly Ala Ala Ile Thr Gly Gly Thr Val Thr Val Glu Gly Cys Gly
275 280 285

Thr Thr Ser Leu Gln Gly Asp Val Lys Phe Ala Glu Val Leu Glu Met
290 295 300

Met Gly Ala Lys Val Thr Trp Thr Asp Thr Ser Val Thr Val Thr Gly
305 310 315 320

Pro Pro Arg Gln Pro Phe Gly Arg Lys His Leu Lys Ala Val Asp Val
325 330 335

Asn Met Asn Lys Met Pro Asp Val Ala Met Thr Leu Ala Val Val Ala
340 345 350

Leu Phe Ala Asp Gly Pro Thr Ala Ile Arg Asp Val Ala Ser Trp Arg
355 360 365

Val Lys Glu Thr Glu Arg Met Val Ala Ile Arg Thr Glu Leu Thr Lys
370 375 380

```
Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
        435                 440                 445

Val Leu Ser Thr Phe Val Lys Asn
    450                 455


<210> SEQ ID NO 21
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide encoding Triticum aestivum EPSPS mutant with
      mutation L216(195)P

<400> SEQUENCE: 21

atggcgacgt ccgtggcggc ccccgcggcg cccgcgggcg ccgaggaggt cgtgctgcag      60

cccatccgcg agatctccgg cgccgtgcag ctgcccggct ccaagtcgct ctccaaccgg     120

atcctcctcc tctccgccct ctccgaggga acaacggtgg tggataacct gttgaacagt     180

gaggatgtcc actacatgct tgaggccctg gaagcccttg gactctccgt ggaagcagat     240

aaagttgcaa aaagagctgt ggttgttggc tgtggcggca ggttcccagt cgaaaaggac     300

gccaaagagg aagtaaagct cttcttgggt aatgctggaa ctgcaatgcg gccactgacg     360

gcagctgtag tagctgctgg tggaaatgca acttatgtgc ttgatggcgt accaagaatg     420

agggagcgac ctattggtga cttagttgta ggtttgcaac aactcggcgc agatgtcgat     480

tgtttccttg gcacaaactg cccacctgtc cgtatcaacg gcaaaggagg tctacctggt     540

ggcaaggtta agctctctgg ttccattagc agtcaatacc tgagttcctt gctgatggct     600

gctcctttgg ctcttgagga tgtcgagatt gaaatcattg ataaaccgat ctccgttcct     660

tatgttgaaa tgacattgaa attgatggag cattttggtg tgactgcgga gcattctgat     720

agttgggaca gattctacat taagggagga caaaaataca agtcccctgg aaatgcctat     780

gtcgaaggtg atgcctcaag tgcgagctat ttcttggctg gtgctgccat caccggaggg     840

actgtgactg tcgaaggttg cggcaccact agtttgcagg gtgatgtgaa atttgctgag     900

gtacttgaaa tgatgggagc aaaggtcaca tggactgaca ctagtgtaac tgttactggc     960

ccaccgcgtc agccatttgg aaggaaacac ctaaaagctg ttgatgtcaa catgaacaaa    1020

atgccagatg tcgcgatgac tctagccgtt gttgccctgt ttgccgatgg tccaaccgct    1080

atcagagatg ttgcctcctg gagagtgaag gaaactgaaa gaatggtcgc gatccggacc    1140

gagctgacga agctgggagc aacggtggag gaaggcccgg actactgcat catcacgccg    1200

ccggagaagc tgaacatcac ggcgatcgac acctacgatg accaccggat ggcgatggcc    1260

ttctccctgg cggcctgtgc tgaggtgcca gtcaccatca gggaccctgg atgcacccga    1320

aagaccttcc ccaactactt cgacgtgcta agcaccttcg tcaagaacta g              1371


<210> SEQ ID NO 22
<211> LENGTH: 456
<212> TYPE: PRT
<213> ORGANISM: Artificial Sequence
<220> FEATURE:
```

-continued

<223> OTHER INFORMATION: Description of Artificial Sequence: Synthetic
      Triticum aestivum EPSPS mutant with mutation L216(195)P
      polypeptide

<400> SEQUENCE: 22

```
Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
            100                 105                 110

Gly Thr Ala Met Arg Pro Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Pro Ile Ser Val Pro Tyr Val Glu Met
    210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Ser Tyr Phe Leu
            260                 265                 270

Ala Gly Ala Ala Ile Thr Gly Gly Thr Val Thr Val Glu Gly Cys Gly
        275                 280                 285

Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380
```

```
Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
        435                 440                 445

Val Leu Ser Thr Phe Val Lys Asn
    450                 455


<210> SEQ ID NO 23
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide encoding Triticum aestivum EPSPS mutant with
      mutations L216(195)P and S269(247)G

<400> SEQUENCE: 23

atggcgacgt ccgtggcggc ccccgcggcg cccgcgggcg ccgaggaggt cgtgctgcag     60

cccatccgcg agatctccgg cgccgtgcag ctgcccggct ccaagtcgct ctccaaccgg    120

atcctcctcc tctccgccct ctccgaggga acaacggtgg tggataacct gttgaacagt    180

gaggatgtcc actacatgct tgaggccctg gaagcccttg gactctccgt ggaagcagat    240

aaagttgcaa aaagagctgt ggttgttggc tgtggcggca ggttcccagt cgaaaaggac    300

gccaaagagg aagtaaagct cttcttgggt aatgctggaa ctgcaatgcg gccactgacg    360

gcagctgtag tagctgctgg tggaaatgca acttatgtgc ttgatggcgt accaagaatg    420

agggagcgac ctattggtga cttagttgta ggtttgcaac aactcggcgc agatgtcgat    480

tgtttccttg gcacaaactg cccacctgtc cgtatcaacg gcaaaggagg tctacctggt    540

ggcaaggtta agctctctgg ttccattagc agtcaatacc tgagttcctt gctgatggct    600

gctcctttgg ctcttgagga tgtcgagatt gaaatcattg ataaaccgat ctccgttcct    660

tatgttgaaa tgacattgaa attgatggag cattttggtg tgactgcgga gcattctgat    720

agttgggaca gattctacat taagggagga caaaaataca agtcccctgg aaatgcctat    780

gtcgaaggtg atgcctcaag tgcgggctat ttcttggctg gtgctgccat caccggaggg    840

actgtgactg tcgaaggttg cggcaccact agtttgcagg gtgatgtgaa atttgctgag    900

gtacttgaaa tgatgggagc aaaggtcaca tggactgaca ctagtgtaac tgttactggc    960

ccaccgcgtc agccatttgg aaggaaacac ctaaaagctg ttgatgtcaa catgaacaaa   1020

atgccagatg tcgcgatgac tctagccgtt gttgccctgt ttgccgatgg tccaaccgct   1080

atcagagatg ttgcctcctg gagagtgaag gaaactgaaa gaatggtcgc gatccggacc   1140

gagctgacga agctgggagc aacggtggag gaaggcccgg actactgcat catcacgccg   1200

ccggagaagc tgaacatcac ggcgatcgac acctacgatg accaccggat ggcgatggcc   1260

ttctccctgg cggcctgtgc tgaggtgcca gtcaccatca gggaccctgg atgcacccga   1320

aagaccttcc ccaactactt cgacgtgcta agcaccttcg tcaagaacta g             1371


<210> SEQ ID NO 24
<211> LENGTH: 456
<212> TYPE: PRT
<213> ORGANISM: Artificial Sequence
```

-continued

<220> FEATURE:
<223> OTHER INFORMATION: Description of Artificial Sequence: Synthetic
Triticum aestivum EPSPS mutant with mutations L216(195)P and
S269(247)G polypeptide

<400> SEQUENCE: 24

```
Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
            100                 105                 110

Gly Thr Ala Met Arg Pro Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Pro Ile Ser Val Pro Tyr Val Glu Met
    210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Gly Tyr Phe Leu
            260                 265                 270

Ala Gly Ala Ala Ile Thr Gly Gly Thr Val Thr Val Glu Gly Cys Gly
        275                 280                 285

Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380
```

```
Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
        435                 440                 445

Val Leu Ser Thr Phe Val Lys Asn
    450                 455


<210> SEQ ID NO 25
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide encoding Triticum aestivum EPSPS mutant with
      mutations L216(195)P, S269(247)G and P118(101)S

<400> SEQUENCE: 25

atggcgacgt ccgtggcggc ccccgcggcg cccgcgggcg ccgaggaggt cgtgctgcag     60

cccatccgcg agatctccgg cgccgtgcag ctgcccggct ccaagtcgct ctccaaccgg    120

atcctcctcc tctccgccct ctccgaggga acaacggtgg tggataacct gttgaacagt    180

gaggatgtcc actacatgct tgaggccctg gaagcccttg gactctccgt ggaagcagat    240

aaagttgcaa aaagagctgt ggttgttggc tgtggcggca ggttcccagt cgaaaaggac    300

gccaaagagg aagtaaagct cttcttgggt aatgctggaa ctgcaatgcg gagcctgacg    360

gcagctgtag tagctgctgg tggaaatgca acttatgtgc ttgatggcgt accaagaatg    420

agggagcgac ctattggtga cttagttgta ggtttgcaac aactcggcgc agatgtcgat    480

tgtttccttg gcacaaactg cccacctgtc cgtatcaacg gcaaaggagg tctacctggt    540

ggcaaggtta agctctctgg ttccattagc agtcaatacc tgagttcctt gctgatggct    600

gctcctttgg ctcttgagga tgtcgagatt gaaatcattg ataaaccgat ctccgttcct    660

tatgttgaaa tgacattgaa attgatggag cattttggtg tgactgcgga gcattctgat    720

agttgggaca gattctacat taagggagga caaaaataca agtcccctgg aaatgcctat    780

gtcgaaggtg atgcctcaag tgcgggctat ttcttggctg gtgctgccat caccggaggg    840

actgtgactg tcgaaggttg cggcaccact agtttgcagg gtgatgtgaa atttgctgag    900

gtacttgaaa tgatgggagc aaaggtcaca tggactgaca ctagtgtaac tgttactggc    960

ccaccgcgtc agccatttgg aaggaaacac ctaaaagctg ttgatgtcaa catgaacaaa   1020

atgccagatg tcgcgatgac tctagccgtt gttgccctgt ttgccgatgg tccaaccgct   1080

atcagagatg ttgcctcctg gagagtgaag gaaactgaaa gaatggtcgc gatccggacc   1140

gagctgacga agctgggagc aacggtggag gaaggcccgg actactgcat catcacgccg   1200

ccggagaagc tgaacatcac ggcgatcgac acctacgatg accaccggat ggcgatggcc   1260

ttctccctgg cggcctgtgc tgaggtgcca gtcaccatca gggaccctgg atgcacccga   1320

aagaccttcc ccaactactt cgacgtgcta agcaccttcg tcaagaacta g             1371


<210> SEQ ID NO 26
<211> LENGTH: 456
<212> TYPE: PRT
<213> ORGANISM: Artificial Sequence
<220> FEATURE:
```

-continued

<223> OTHER INFORMATION: Description of Artificial Sequence: Synthetic Triticum aestivum EPSPS mutant with mutations L216(195)P, S269(247)G and P118(101)S polypeptide

<400> SEQUENCE: 26

```
Met Ala Thr Ser Val Ala Ala Pro Ala Ala Pro Ala Gly Ala Glu Glu
1               5                   10                  15

Val Val Leu Gln Pro Ile Arg Glu Ile Ser Gly Ala Val Gln Leu Pro
            20                  25                  30

Gly Ser Lys Ser Leu Ser Asn Arg Ile Leu Leu Leu Ser Ala Leu Ser
        35                  40                  45

Glu Gly Thr Thr Val Val Asp Asn Leu Leu Asn Ser Glu Asp Val His
    50                  55                  60

Tyr Met Leu Glu Ala Leu Glu Ala Leu Gly Leu Ser Val Glu Ala Asp
65                  70                  75                  80

Lys Val Ala Lys Arg Ala Val Val Val Gly Cys Gly Gly Arg Phe Pro
                85                  90                  95

Val Glu Lys Asp Ala Lys Glu Glu Val Lys Leu Phe Leu Gly Asn Ala
            100                 105                 110

Gly Thr Ala Met Arg Ser Leu Thr Ala Ala Val Val Ala Ala Gly Gly
        115                 120                 125

Asn Ala Thr Tyr Val Leu Asp Gly Val Pro Arg Met Arg Glu Arg Pro
    130                 135                 140

Ile Gly Asp Leu Val Val Gly Leu Gln Gln Leu Gly Ala Asp Val Asp
145                 150                 155                 160

Cys Phe Leu Gly Thr Asn Cys Pro Pro Val Arg Ile Asn Gly Lys Gly
                165                 170                 175

Gly Leu Pro Gly Gly Lys Val Lys Leu Ser Gly Ser Ile Ser Ser Gln
            180                 185                 190

Tyr Leu Ser Ser Leu Leu Met Ala Ala Pro Leu Ala Leu Glu Asp Val
        195                 200                 205

Glu Ile Glu Ile Ile Asp Lys Pro Ile Ser Val Pro Tyr Val Glu Met
    210                 215                 220

Thr Leu Lys Leu Met Glu His Phe Gly Val Thr Ala Glu His Ser Asp
225                 230                 235                 240

Ser Trp Asp Arg Phe Tyr Ile Lys Gly Gly Gln Lys Tyr Lys Ser Pro
                245                 250                 255

Gly Asn Ala Tyr Val Glu Gly Asp Ala Ser Ser Ala Gly Tyr Phe Leu
            260                 265                 270

Ala Gly Ala Ala Ile Thr Gly Gly Thr Val Thr Val Glu Gly Cys Gly
        275                 280                 285

Thr Thr Ser Leu Gln Gly Asp Val Lys Phe Ala Glu Val Leu Glu Met
    290                 295                 300

Met Gly Ala Lys Val Thr Trp Thr Asp Thr Ser Val Thr Val Thr Gly
305                 310                 315                 320

Pro Pro Arg Gln Pro Phe Gly Arg Lys His Leu Lys Ala Val Asp Val
                325                 330                 335

Asn Met Asn Lys Met Pro Asp Val Ala Met Thr Leu Ala Val Val Ala
            340                 345                 350

Leu Phe Ala Asp Gly Pro Thr Ala Ile Arg Asp Val Ala Ser Trp Arg
        355                 360                 365

Val Lys Glu Thr Glu Arg Met Val Ala Ile Arg Thr Glu Leu Thr Lys
    370                 375                 380
```

-continued

```
Leu Gly Ala Thr Val Glu Glu Gly Pro Asp Tyr Cys Ile Ile Thr Pro
385                 390                 395                 400

Pro Glu Lys Leu Asn Ile Thr Ala Ile Asp Thr Tyr Asp Asp His Arg
                405                 410                 415

Met Ala Met Ala Phe Ser Leu Ala Ala Cys Ala Glu Val Pro Val Thr
            420                 425                 430

Ile Arg Asp Pro Gly Cys Thr Arg Lys Thr Phe Pro Asn Tyr Phe Asp
        435                 440                 445

Val Leu Ser Thr Phe Val Lys Asn
    450                 455


<210> SEQ ID NO 27
<211> LENGTH: 1365
<212> TYPE: DNA
<213> ORGANISM: Oryza sativa

<400> SEQUENCE: 27

atggcgtcca acgccgcggc tgcggcggcg aaggcggagg agatcgtgct ccagcccatc      60

agggagatct ccggggcggt tcagctgcca gggtccaagt cgctctccaa caggatcctc     120

ctcctctccg ccctctccga gggcacaaca gtggtggaca acttgctgaa cagtgaggat     180

gttcactaca tgcttgaggc cctgaaagcc ctcgggctct ctgtggaagc agataaagtt     240

gcaaaaagag ctgtagtcgt tggctgtggt ggcaagtttc ctgttgagaa ggatgcgaaa     300

gaggaagtgc aactcttctt ggggaacgct ggaactgcaa tgcgaccatt gacagcagcc     360

gtgactgctg ctggtggaaa tgcaacttat gtgcttgatg gagtgccacg aatgagggag     420

agaccgattg gtgacttggt tgtcgggttg aaacaacttg gtgcggatgt cgactgtttc     480

cttggcactg aatgcccacc tgttcgtgtc aagggaattg gaggacttcc tggtggcaag     540

gttaagctct ctggttccat cagcagtcag tacttgagtg ccttgctgat ggctgctcct     600

ttggcccttg gggatgtgga gatcgaaatc attgacaaac taatctccat tccttacgtt     660

gaaatgacat tgagattgat ggagcgtttt ggtgtgaagg cagagcattc tgatagttgg     720

gacagattct atattaaggg agggcagaag tacaaatctc ctggaaatgc ctatgttgaa     780

ggtgatgcct caagcgcgag ctatttcttg gctggtgctg caatcactgg aggcactgtg     840

acagttcaag gttgtggtac gaccagtttg cagggtgatg tcaaatttgc tgaggtactt     900

gagatgatgg gagcaaaggt tacatggact gacaccagtg taaccgtaac tggtccacca     960

cgtgagcctt atgggaagaa acacctgaaa gctgttgatg tcaacatgaa caaaatgcct    1020

gatgttgcca tgacccttgc cgttgttgca ctcttcgctg atggtccaac tgctatcaga    1080

gatgtggctt cctggagagt aaaggaaacc gaaaggatgg ttgcaattcg gaccgagcta    1140

acaaagctgg gagcatcggt tgaagaaggt cctgactact gcatcatcac cccaccggag    1200

aagctgaaca tcacggcaat cgacacctac gatgatcaca ggatggccat ggccttctcc    1260

ctcgctgcct gcgccgacgt gcccgtgacg atcagggacc ctggttgcac ccgcaagacc    1320

ttccccaact acttcgacgt tctaagcact ttcgtcagga actga                    1365


<210> SEQ ID NO 28
<211> LENGTH: 454
<212> TYPE: PRT
<213> ORGANISM: Oryza sativa
```

<400> SEQUENCE: 28

Met Ala Ser Asn Ala Ala Ala Ala Ala Ala Lys Ala Glu Glu Ile Val
1 5 10 15

Leu Gln Pro Ile Arg Glu Ile Ser Gly Ala Val Gln Leu Pro Gly Ser
20 25 30

Lys Ser Leu Ser Asn Arg Ile Leu Leu Leu Ser Ala Leu Ser Glu Gly
35 40 45

Thr Thr Val Val Asp Asn Leu Leu Asn Ser Glu Asp Val His Tyr Met
50 55 60

Leu Glu Ala Leu Lys Ala Leu Gly Leu Ser Val Glu Ala Asp Lys Val
65 70 75 80

Ala Lys Arg Ala Val Val Val Gly Cys Gly Gly Lys Phe Pro Val Glu
85 90 95

Lys Asp Ala Lys Glu Glu Val Gln Leu Phe Leu Gly Asn Ala Gly Thr
100 105 110

Ala Met Arg Pro Leu Thr Ala Ala Val Thr Ala Ala Gly Gly Asn Ala
115 120 125

Thr Tyr Val Leu Asp Gly Val Pro Arg Met Arg Glu Arg Pro Ile Gly
130 135 140

Asp Leu Val Val Gly Leu Lys Gln Leu Gly Ala Asp Val Asp Cys Phe
145 150 155 160

Leu Gly Thr Glu Cys Pro Pro Val Arg Val Lys Gly Ile Gly Gly Leu
165 170 175

Pro Gly Gly Lys Val Lys Leu Ser Gly Ser Ile Ser Ser Gln Tyr Leu
180 185 190

Ser Ala Leu Leu Met Ala Ala Pro Leu Ala Leu Gly Asp Val Glu Ile
195 200 205

Glu Ile Ile Asp Lys Leu Ile Ser Ile Pro Tyr Val Glu Met Thr Leu
210 215 220

Arg Leu Met Glu Arg Phe Gly Val Lys Ala Glu His Ser Asp Ser Trp
225 230 235 240

Asp Arg Phe Tyr Ile Lys Gly Gly Gln Lys Tyr Lys Ser Pro Gly Asn
245 250 255

Ala Tyr Val Glu Gly Asp Ala Ser Ser Ala Ser Tyr Phe Leu Ala Gly
260 265 270

Ala Ala Ile Thr Gly Gly Thr Val Thr Val Gln Gly Cys Gly Thr Thr
275 280 285

Ser Leu Gln Gly Asp Val Lys Phe Ala Glu Val Leu Glu Met Met Gly
290 295 300

Ala Lys Val Thr Trp Thr Asp Thr Ser Val Thr Val Thr Gly Pro Pro
305 310 315 320

Arg Glu Pro Tyr Gly Lys Lys His Leu Lys Ala Val Asp Val Asn Met
325 330 335

Asn Lys Met Pro Asp Val Ala Met Thr Leu Ala Val Val Ala Leu Phe
340 345 350

Ala Asp Gly Pro Thr Ala Ile Arg Asp Val Ala Ser Trp Arg Val Lys
355 360 365

Glu Thr Glu Arg Met Val Ala Ile Arg Thr Glu Leu Thr Lys Leu Gly
370 375 380

Ala Ser Val Glu Glu Gly Pro Asp Tyr Cys Ile Ile Thr Pro Pro Glu
385 390 395 400

```
Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450
```

```
<210> SEQ ID NO 29
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide encoding Oryza sativa EPSPS mutant with mutation
      L214(195)P

<400> SEQUENCE: 29

atggcgtcca acgccgcggc tgcggcggcg aaggcggagg agatcgtgct ccagcccatc      60

agggagatct ccggggcggt tcagctgcca gggtccaagt cgctctccaa caggatcctc     120

ctcctctccg ccctctccga gggcacaaca gtggtggaca acttgctgaa cagtgaggat     180

gttcactaca tgcttgaggc cctgaaagcc ctcgggctct ctgtggaagc agataaagtt     240

gcaaaaagag ctgtagtcgt tggctgtggt ggcaagtttc ctgttgagaa ggatgcgaaa     300

gaggaagtgc aactcttctt ggggaacgct ggaactgcaa tgcgaccatt gacagcagcc     360

gtgactgctg ctggtggaaa tgcaacttat gtgcttgatg gagtgccacg aatgagggag     420

agaccgattg gtgacttggt tgtcgggttg aaacaacttg gtgcggatgt cgactgtttc     480

cttggcactg aatgcccacc tgttcgtgtc aagggaattg gaggacttcc tggtggcaag     540

gttaagctct ctggttccat cagcagtcag tacttgagtg ccttgctgat ggctgctcct     600

ttggcccttg ggatgtgga gatcgaaatc attgacaaac cgatctccat tccttacgtt      660

gaaatgacat tgagattgat ggagcgtttt ggtgtgaagg cagagcattc tgatagttgg     720

gacagattct atattaaggg agggcagaag tacaaatctc ctggaaatgc ctatgttgaa     780

ggtgatgcct caagcgcgag ctatttcttg gctggtgctg caatcactgg aggcactgtg     840

acagttcaag gttgtggtac gaccagtttg cagggtgatg tcaaatttgc tgaggtactt     900

gagatgatgg gagcaaaggt tacatggact gacaccagtg taaccgtaac tggtccacca     960

cgtgagcctt atgggaagaa acacctgaaa gctgttgatg tcaacatgaa caaaatgcct    1020

gatgttgcca tgacccttgc cgttgttgca ctcttcgctg atggtccaac tgctatcaga    1080

gatgtggctt cctggagagt aaaggaaacc gaaaggatgg ttgcaattcg gaccgagcta    1140

acaaagctgg gagcatcggt tgaagaaggt cctgactact gcatcatcac cccaccggag    1200

aagctgaaca tcacggcaat cgacacctac gatgatcaca ggatggccat ggccttctcc    1260

ctcgctgcct gcgccgacgt gcccgtgacg atcagggacc ctggttgcac ccgcaagacc    1320

ttccccaact acttcgacgt tctaagcact ttcgtcagga actga                    1365
```

```
<210> SEQ ID NO 30
<211> LENGTH: 454
<212> TYPE: PRT
<213> ORGANISM: Artificial Sequence
<220> FEATURE:
```

```
<223> OTHER INFORMATION: Description of Artificial Sequence: Synthetic
      Oryza sativa EPSPS mutant with mutation L214(195)P
      polypeptide

<400> SEQUENCE: 30

Met Ala Ser Asn Ala Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Pro Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Pro Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450


<210> SEQ ID NO 31
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide encoding Oryza sativa EPSPS mutant with mutation
      P116(101)S

<400> SEQUENCE: 31

atggcgtcca acgccgcggc tgcggcggcg aaggcggagg agatcgtgct ccagcccatc     60

agggagatct ccggggcggt tcagctgcca gggtccaagt cgctctccaa caggatcctc    120

ctcctctccg ccctctccga gggcacaaca gtggtggaca acttgctgaa cagtgaggat    180

gttcactaca tgcttgaggc cctgaaagcc ctcgggctct ctgtggaagc agataaagtt    240

gcaaaaagag ctgtagtcgt tggctgtggt ggcaagtttc ctgttgagaa ggatgcgaaa    300

gaggaagtgc aactcttctt ggggaacgct ggaactgcaa tgcgatcctt gacagcagcc    360

gtgactgctg ctggtggaaa tgcaacttat gtgcttgatg gagtgccacg aatgagggag    420

agaccgattg gtgacttggt tgtcgggttg aaacaacttg gtgcggatgt cgactgtttc    480

cttggcactg aatgcccacc tgttcgtgtc aagggaattg gaggacttcc tggtggcaag    540

gttaagctct ctggttccat cagcagtcag tacttgagtg ccttgctgat ggctgctcct    600

ttggcccttg gggatgtgga gatcgaaatc attgacaaac taatctccat tccttacgtt    660

gaaatgacat tgagattgat ggagcgtttt ggtgtgaagg cagagcattc tgatagttgg    720

gacagattct atattaaggg agggcagaag tacaaatctc ctggaaatgc ctatgttgaa    780

ggtgatgcct caagcgcgag ctatttcttg gctggtgctg caatcactgg aggcactgtg    840

acagttcaag gttgtggtac gaccagtttg cagggtgatg tcaaatttgc tgaggtactt    900

gagatgatgg gagcaaaggt tacatggact gacaccagtg taaccgtaac tggtccacca    960

cgtgagcctt atggaagaa acacctgaaa gctgttgatg tcaacatgaa caaaatgcct   1020

gatgttgcca tgacccttgc cgttgttgca ctcttcgctg atggtccaac tgctatcaga   1080

gatgtggctt cctggagagt aaaggaaacc gaaaggatgg ttgcaattcg gaccgagcta   1140

acaaagctgg gagcatcggt tgaagaaggt cctgactact gcatcatcac ccccaccggag   1200

aagctgaaca tcacggcaat cgacacctac gatgatcaca ggatggccat ggccttctcc   1260

ctcgctgcct gcgccgacgt gcccgtgacg atcagggacc ctggttgcac ccgcaagacc   1320

ttccccaact acttcgacgt tctaagcact ttcgtcagga actga                    1365


<210> SEQ ID NO 32
<211> LENGTH: 454
<212> TYPE: PRT
<213> ORGANISM: Artificial Sequence
```

```
<220> FEATURE:
<223> OTHER INFORMATION: Description of Artificial Sequence: Synthetic
      Oryza sativa EPSPS mutant with mutation P116(101)S
      polypeptide

<400> SEQUENCE: 32

Met Ala Ser Asn Ala Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Ser Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

-continued

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450
```

<210> SEQ ID NO 33
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide encoding Oryza sativa EPSPS mutant with mutations L214(195)P and P116(101)S

<400> SEQUENCE: 33

```
atggcgtcca acgccgcggc tgcggcggcg aaggcggagg agatcgtgct ccagcccatc     60

agggagatct ccggggcggt tcagctgcca gggtccaagt cgctctccaa caggatcctc    120

ctcctctccg ccctctccga gggcacaaca gtggtggaca acttgctgaa cagtgaggat    180

gttcactaca tgcttgaggc cctgaaagcc ctcgggctct ctgtggaagc agataaagtt    240

gcaaaaagag ctgtagtcgt tggctgtggt ggcaagtttc ctgttgagaa ggatgcgaaa    300

gaggaagtgc aactcttctt ggggaacgct ggaactgcaa tgcgatcctt gacagcagcc    360

gtgactgctg ctggtggaaa tgcaacttat gtgcttgatg gagtgccacg aatgagggag    420

agaccgattg gtgacttggt tgtcgggttg aaacaacttg gtgcggatgt cgactgtttc    480

cttggcactg aatgcccacc tgttcgtgtc aagggaattg gaggacttcc tggtggcaag    540

gttaagctct ctggttccat cagcagtcag tacttgagtg ccttgctgat ggctgctcct    600

ttggcccttg gggatgtgga gatcgaaatc attgacaaac cgatctccat tccttacgtt    660

gaaatgacat tgagattgat ggagcgtttt ggtgtgaagg cagagcattc tgatagttgg    720

gacagattct atattaaggg agggcagaag tacaaatctc ctggaaatgc ctatgttgaa    780

ggtgatgcct caagcgcgag ctatttcttg gctggtgctg caatcactgg aggcactgtg    840

acagttcaag gttgtggtac gaccagtttg cagggtgatg tcaaatttgc tgaggtactt    900

gagatgatgg gagcaaaggt tacatggact gacaccagtg taaccgtaac tggtccacca    960

cgtgagcctt atgggaagaa acacctgaaa gctgttgatg tcaacatgaa caaaatgcct   1020

gatgttgcca tgacccttgc cgttgttgca ctcttcgctg atggtccaac tgctatcaga   1080

gatgtggctt cctggagagt aaaggaaacc gaaaggatgg ttgcaattcg gaccgagcta   1140

acaaagctgg gagcatcggt tgaagaaggt cctgactact gcatcatcac cccaccggag   1200

aagctgaaca tcacggcaat cgacacctac gatgatcaca ggatggccat ggccttctcc   1260

ctcgctgcct gcgccgacgt gcccgtgacg atcagggacc ctggttgcac ccgcaagacc   1320

ttccccaact acttcgacgt tctaagcact ttcgtcagga actga                    1365
```

<210> SEQ ID NO 34
<211> LENGTH: 454
<212> TYPE: PRT
<213> ORGANISM: Artificial Sequence
<220> FEATURE:

```
<223> OTHER INFORMATION: Description of Artificial Sequence: Synthetic
      Oryza sativa EPSPS mutant with mutations L214(195)P and
      P116(101)S polypeptide

<400> SEQUENCE: 34

Met Ala Ser Asn Ala Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Ser Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Pro Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450


<210> SEQ ID NO 35
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide encoding Oryza sativa EPSPS mutant with mutation
      S267(247)G

<400> SEQUENCE: 35

atggcgtcca acgccgcggc tgcggcggcg aaggcggagg agatcgtgct ccagcccatc     60

agggagatct ccggggcggt tcagctgcca gggtccaagt cgctctccaa caggatcctc    120

ctcctctccg ccctctccga gggcacaaca gtggtggaca acttgctgaa cagtgaggat    180

gttcactaca tgcttgaggc cctgaaagcc ctcgggctct ctgtggaagc agataaagtt    240

gcaaaaagag ctgtagtcgt tggctgtggt ggcaagtttc ctgttgagaa ggatgcgaaa    300

gaggaagtgc aactcttctt ggggaacgct ggaactgcaa tgcgaccatt gacagcagcc    360

gtgactgctg ctggtggaaa tgcaacttat gtgcttgatg gagtgccacg aatgagggag    420

agaccgattg gtgacttggt tgtcgggttg aaacaacttg gtgcggatgt cgactgtttc    480

cttggcactg aatgcccacc tgttcgtgtc aagggaattg gaggacttcc tggtggcaag    540

gttaagctct ctggttccat cagcagtcag tacttgagtg ccttgctgat ggctgctcct    600

ttggcccttg gggatgtgga gatcgaaatc attgacaaac taatctccat tccttacgtt    660

gaaatgacat tgagattgat ggagcgtttt ggtgtgaagg cagagcattc tgatagttgg    720

gacagattct atattaaggg agggcagaag tacaaatctc ctggaaatgc ctatgttgaa    780

ggtgatgcct caagcgcggg ctatttcttg gctggtgctg caatcactgg aggcactgtg    840

acagttcaag gttgtggtac gaccagtttg cagggtgatg tcaaatttgc tgaggtactt    900

gagatgatgg gagcaaaggt tacatggact gacaccagtg taaccgtaac tggtccacca    960

cgtgagcctt atggaagaa acacctgaaa gctgttgatg tcaacatgaa caaaatgcct   1020

gatgttgcca tgacccttgc cgttgttgca ctcttcgctg atggtccaac tgctatcaga   1080

gatgtggctt cctggagagt aaaggaaacc gaaaggatgg ttgcaattcg gaccgagcta   1140

acaaagctgg gagcatcggt tgaagaaggt cctgactact gcatcatcac cccaccggag   1200

aagctgaaca tcacggcaat cgacacctac gatgatcaca ggatggccat ggccttctcc   1260

ctcgctgcct gcgccgacgt gcccgtgacg atcagggacc ctggttgcac ccgcaagacc   1320

ttccccaact acttcgacgt tctaagcact ttcgtcagga actga                   1365


<210> SEQ ID NO 36
<211> LENGTH: 454
<212> TYPE: PRT
<213> ORGANISM: Artificial Sequence
```

```
<220> FEATURE:
<223> OTHER INFORMATION: Description of Artificial Sequence: Synthetic
      Oryza sativa EPSPS mutant with mutation S267(247)G
      polypeptide

<400> SEQUENCE: 36

Met Ala Ser Asn Ala Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Pro Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Gly Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450


<210> SEQ ID NO 37
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide encoding Oryza sativa EPSPS mutant with mutations
      S267(247)G and P116(101)S

<400> SEQUENCE: 37

atggcgtcca acgccgcggc tgcggcggcg aaggcggagg agatcgtgct ccagcccatc     60

agggagatct ccggggcggt tcagctgcca gggtccaagt cgctctccaa caggatcctc    120

ctcctctccg ccctctccga gggcacaaca gtggtggaca acttgctgaa cagtgaggat    180

gttcactaca tgcttgaggc cctgaaagcc ctcgggctct ctgtggaagc agataaagtt    240

gcaaaaagag ctgtagtcgt tggctgtggt ggcaagtttc ctgttgagaa ggatgcgaaa    300

gaggaagtgc aactcttctt ggggaacgct ggaactgcaa tgcgatcctt gacagcagcc    360

gtgactgctg ctggtggaaa tgcaacttat gtgcttgatg gagtgccacg aatgagggag    420

agaccgattg gtgacttggt tgtcgggttg aaacaacttg gtgcggatgt cgactgtttc    480

cttggcactg aatgcccacc tgttcgtgtc aagggaattg gaggacttcc tggtggcaag    540

gttaagctct ctggttccat cagcagtcag tacttgagtg ccttgctgat ggctgctcct    600

ttggcccttg gggatgtgga gatcgaaatc attgacaaac taatctccat tccttacgtt    660

gaaatgacat tgagattgat ggagcgtttt ggtgtgaagg cagagcattc tgatagttgg    720

gacagattct atattaaggg agggcagaag tacaaatctc ctggaaatgc ctatgttgaa    780

ggtgatgcct caagcgcggg ctatttcttg gctggtgctg caatcactgg aggcactgtg    840

acagttcaag gttgtggtac gaccagtttg cagggtgatg tcaaatttgc tgaggtactt    900

gagatgatgg gagcaaaggt tacatggact gacaccagtg taaccgtaac tggtccacca    960

cgtgagcctt atgggaagaa acacctgaaa gctgttgatg tcaacatgaa caaaatgcct   1020

gatgttgcca tgacccttgc cgttgttgca ctcttcgctg atggtccaac tgctatcaga   1080

gatgtggctt cctggagagt aaaggaaacc gaaaggatgg ttgcaattcg gaccgagcta   1140

acaaagctgg gagcatcggt tgaagaaggt cctgactact gcatcatcac cccaccggag   1200

aagctgaaca tcacggcaat cgacacctac gatgatcaca ggatggccat ggccttctcc   1260

ctcgctgcct gcgccgacgt gcccgtgacg atcagggacc ctggttgcac ccgcaagacc   1320

ttccccaact acttcgacgt tctaagcact ttcgtcagga actga                    1365


<210> SEQ ID NO 38
<211> LENGTH: 454
<212> TYPE: PRT
<213> ORGANISM: Artificial Sequence
<220> FEATURE:
```

-continued

<223> OTHER INFORMATION: Description of Artificial Sequence: Synthetic
      Oryza sativa EPSPS mutant with mutations S267(247)G and
      P116(101)S polypeptide

<400> SEQUENCE: 38

```
Met Ala Ser Asn Ala Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Ser Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Leu Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Gly Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

-continued

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450
```

<210> SEQ ID NO 39
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide encoding Oryza sativa EPSPS mutant with mutations S267(247)G, L214(195)P and P116(101)S

<400> SEQUENCE: 39

```
atggcgtcca acgccgcggc tgcggcggcg aaggcggagg agatcgtgct ccagcccatc     60

agggagatct ccggggcggt tcagctgcca gggtccaagt cgctctccaa caggatcctc    120

ctcctctccg ccctctccga gggcacaaca gtggtggaca acttgctgaa cagtgaggat    180

gttcactaca tgcttgaggc cctgaaagcc ctcgggctct ctgtggaagc agataaagtt    240

gcaaaaagag ctgtagtcgt tggctgtggt ggcaagtttc ctgttgagaa ggatgcgaaa    300

gaggaagtgc aactcttctt ggggaacgct ggaactgcaa tgcgatcctt gacagcagcc    360

gtgactgctg ctggtggaaa tgcaacttat gtgcttgatg gagtgccacg aatgagggag    420

agaccgattg gtgacttggt tgtcgggttg aaacaacttg gtgcggatgt cgactgtttc    480

cttggcactg aatgcccacc tgttcgtgtc aagggaattg gaggacttcc tggtggcaag    540

gttaagctct ctggttccat cagcagtcag tacttgagtg ccttgctgat ggctgctcct    600

ttggcccttg gggatgtgga gatcgaaatc attgacaaac cgatctccat tccttacgtt    660

gaaatgacat tgagattgat ggagcgtttt ggtgtgaagg cagagcattc tgatagttgg    720

gacagattct atattaaggg agggcagaag tacaaatctc ctggaaatgc ctatgttgaa    780

ggtgatgcct caagcgcggg ctatttcttg gctggtgctg caatcactgg aggcactgtg    840

acagttcaag gttgtggtac gaccagtttg cagggtgatg tcaaatttgc tgaggtactt    900

gagatgatgg gagcaaaggt tacatggact gacaccagtg taaccgtaac tggtccacca    960

cgtgagcctt atggaagaa acacctgaaa gctgttgatg tcaacatgaa caaaatgcct   1020

gatgttgcca tgacccttgc cgttgttgca ctcttcgctg atggtccaac tgctatcaga   1080

gatgtggctt cctggagagt aaaggaaacc gaaaggatgg ttgcaattcg gaccgagcta   1140

acaaagctgg gagcatcggt tgaagaaggt cctgactact gcatcatcac cccaccggag   1200

aagctgaaca tcacggcaat cgacacctac gatgatcaca ggatggccat ggccttctcc   1260

ctcgctgcct gcgccgacgt gcccgtgacg atcagggacc ctggttgcac ccgcaagacc   1320

ttccccaact acttcgacgt tctaagcact ttcgtcagga actga                  1365
```

<210> SEQ ID NO 40
<211> LENGTH: 454
<212> TYPE: PRT
<213> ORGANISM: Artificial Sequence

```
<220> FEATURE:
<223> OTHER INFORMATION: Description of Artificial Sequence: Synthetic
      Oryza sativa EPSPS mutant with mutations S267(247)G,
      L214(195)P and P116(101)S polypeptide

<400> SEQUENCE: 40

Met Ala Ser Asn Ala Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30

Lys Ser Leu Ser Asn Arg Ile Leu Leu Leu Ser Ala Leu Ser Glu Gly
        35                  40                  45

Thr Thr Val Val Asp Asn Leu Leu Asn Ser Glu Asp Val His Tyr Met
    50                  55                  60

Leu Glu Ala Leu Lys Ala Leu Gly Leu Ser Val Glu Ala Asp Lys Val
65                  70                  75                  80

Ala Lys Arg Ala Val Val Val Gly Cys Gly Gly Lys Phe Pro Val Glu
                85                  90                  95

Lys Asp Ala Lys Glu Glu Val Gln Leu Phe Leu Gly Asn Ala Gly Thr
            100                 105                 110

Ala Met Arg Ser Leu Thr Ala Ala Val Thr Ala Ala Gly Gly Asn Ala
        115                 120                 125

Thr Tyr Val Leu Asp Gly Val Pro Arg Met Arg Glu Arg Pro Ile Gly
    130                 135                 140

Asp Leu Val Val Gly Leu Lys Gln Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
            180                 185                 190

Ser Ala Leu Leu Met Ala Ala Pro Leu Ala Leu Gly Asp Val Glu Ile
        195                 200                 205

Glu Ile Ile Asp Lys Pro Ile Ser Ile Pro Tyr Val Glu Met Thr Leu
    210                 215                 220

Arg Leu Met Glu Arg Phe Gly Val Lys Ala Glu His Ser Asp Ser Trp
225                 230                 235                 240

Asp Arg Phe Tyr Ile Lys Gly Gly Gln Lys Tyr Lys Ser Pro Gly Asn
                245                 250                 255

Ala Tyr Val Glu Gly Asp Ala Ser Ser Ala Gly Tyr Phe Leu Ala Gly
            260                 265                 270

Ala Ala Ile Thr Gly Gly Thr Val Thr Val Gln Gly Cys Gly Thr Thr
        275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Val Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380
```

```
Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415

Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450


<210> SEQ ID NO 41
<211> LENGTH: 427
<212> TYPE: PRT
<213> ORGANISM: Escherichia coli

<400> SEQUENCE: 41

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300
```

```
Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
            420                 425


<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

ggtggctcct acaaatgcca tc                                              22


<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

gagccaatta acgtcatccc ac                                              22


<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

gcttctgacc agcccattat tctgc                                           25


<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

ccctcaaggg taagctcatc tctcttc                                         27
```